(12) United States Patent
Cuberes-Altisent et al.

(10) Patent No.: US 8,202,872 B2
(45) Date of Patent: *Jun. 19, 2012

(54) PYRAZOLE DERIVATIVES AS SIGMA RECEPTOR INHIBITORS

(75) Inventors: Rosa Cuberes-Altisent, Barcelona (ES); Joerg Holenz, Barcelona (ES)

(73) Assignee: Laboratorios del Dr. Esteve, S.A., Barcelona (ES)

( * ) Notice: Subject to any disclaimer, the term of this patent is extended or adjusted under 35 U.S.C. 154(b) by 592 days.

This patent is subject to a terminal disclaimer.

(21) Appl. No.: 12/281,313

(22) PCT Filed: Mar. 1, 2007

(86) PCT No.: PCT/EP2007/001795
§ 371 (c)(1),
(2), (4) Date: Jan. 28, 2009

(87) PCT Pub. No.: WO2007/098953
PCT Pub. Date: Sep. 7, 2007

(65) Prior Publication Data
US 2009/0264442 A1 Oct. 22, 2009

(30) Foreign Application Priority Data

Mar. 1, 2006 (EP) .................................. 06004079
Mar. 1, 2006 (EP) .................................. 06004080
Mar. 1, 2006 (EP) .................................. 06004081

(51) Int. Cl.
*A61K 31/496* (2006.01)
*A61K 31/454* (2006.01)
*A61K 31/437* (2006.01)
*C07D 401/12* (2006.01)
*C07D 221/00* (2006.01)

(52) U.S. Cl. .............. 514/254.05; 514/303; 514/326; 544/371; 546/118; 546/211

(58) Field of Classification Search .................. None
See application file for complete search history.

(56) References Cited

FOREIGN PATENT DOCUMENTS

| EP | 0 414 289 B1 | 2/1991 |
| EP | 0 445 974 A2 | 9/1991 |
| EP | 0 518 805 A1 | 12/1992 |
| FR | 2 472 564 * | 7/1981 |
| WO | 02/102387 A1 | 12/2002 |
| WO | WO 2006/015842 * | 2/2006 |
| WO | WO 2006/021462 * | 3/2006 |

OTHER PUBLICATIONS

Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Wolff et al. Burger's Medicinal Chemistry and Drug Discovery. 5th ed. vol. 1: Principles and Practice (1995). pp. 975-977.*
Morissette et al. "High-throughput crystallization: polymorphs, salts, co-crystals and solvates of pharmaceutical solids." Advanced Drug Delivery Reviews 2004, 56, 275-300.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta, Sudha R. "Crystalline Solids." Advanced Drug Delivery Reviews 48(2001): 3-26.*

* cited by examiner

*Primary Examiner* — Rebecca Anderson
*Assistant Examiner* — Alicia L Otton
(74) *Attorney, Agent, or Firm* — Heslin Rothenberg Farley & Mesiti P.C.; Andrew K. Gonsalves

(57) ABSTRACT

The invention relates to compounds of formula I

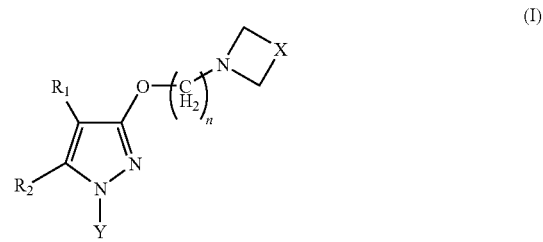

(I)

having pharmacological activity towards the sigma receptor, to processes of preparation of such compounds, to pharmaceutical compositions comprising them, and to their use for the treatment and or prophylaxis of a disease in which the sigma receptor is involved.

20 Claims, No Drawings great effort has been directed to find selective ligands. Thus, the prior art discloses different sigma receptor ligands.

PYRAZOLE DERIVATIVES AS SIGMA RECEPTOR INHIBITORS

CROSS REFERENCE TO RELATED APPLICATIONS

This application is a U.S. National Phase filing under 35 U.S.C. §371 of International Application PCT/EP2007/001795, filed Mar. 1, 2007, and published as WO 2007/098953 on Sep. 7, 2007. PCT/EP2007/001795 claimed benefit of priority from European Patent Application Nos. EP 0-600-4079.7, EP 0-600-4080.5, and EP 0-600-4081.3, all filed on Mar. 1, 2006. The entire contents of each of the prior applications are incorporated herein by reference.

FIELD OF THE INVENTION

The present invention relates to compounds having pharmacological activity towards the sigma (σ) receptor, and more particularly to some pyrazole derivatives, to processes of preparation of such compounds, to pharmaceutical compositions comprising them, and to their use in therapy and prophylaxis, in particular for the treatment of psychosis.

BACKGROUND OF THE INVENTION

The search for new therapeutic agents has been greatly aided in recent years by better understanding of the structure of proteins and other biomolecules associated with target diseases. One important class of these proteins is the sigma (σ) receptor, a cell surface receptor of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, *Pharmacological Reviews*, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)SKF 10047, (+)cyclazocine, and (+)pentazocine and also for some narcoleptics such as haloperidol.

The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma (σ-2) site. Haloperidol has similar affinities for both subtypes. Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. *Trends Pharmacol. Sci.*, 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. *Proc. Natl. Acad. Sci.*, 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands.

International Patent Application WO 91/09594 generically describes a broad class of sigma receptor ligands some of which are 4-phenylpiperidine, -tetrahydro-pyridine or -piperazine compounds having an optionally substituted aryl or heteroaryl, alkyl, alkenyl, alkynyl, alkoxy or alkoxyalkyl substituent on the ring N-atom. The terms aryl and heteroaryl are defined by mention of a number of such substituents.

European patent application EP 0 414 289 A1 generically discloses a class of 1,2,3,4-tetrahydro-spiro[naphthalene-1,4'-piperidine] and 1,4-dihydro-spiro[naphthalene-1,4'-piperidine] derivatives substituted at the piperidine N-atom with a hydrocarbon group alleged to have selective sigma receptor antagonistic activity. The term hydrocarbon, as defined in said patent, covers all possible straight chained, cyclic, heterocyclic, etc. groups. However, only compounds having benzyl, phenethyl, cycloalkylmethyl, furyl- or thienylmethyl or lower alkyl or alkenyl as the hydrocarbon substituent at the piperidine nitrogen atom are specifically disclosed. The compounds are stated to displace tritiated di-tolyl guanidine (DTG) from sigma sites with potencies better than 200 nM. 1'-benzyl-1,2,3,4-tetrahydro-spiro[naphthalene-1,4'-piperidine] is mentioned as a particularly preferred compound.

European patent application EP 0 445 974 A2 generically describes the corresponding spiro[indane-1,4'-piperidine] and spiro[benzocycloheptene-5,4'-piperidine] derivatives. Again the compounds are only stated to displace tritiated di-tolyl guanidine (DTG) from sigma sites with potencies better than 200 nM.

European patent Application EP0 431 943 A relates to a further extremely broad class of spiropiperidine compounds substituted at the piperidine N-atom and claimed to be useful as antiarrhythmics and for impaired cardiac pump function. The said application exemplifies several compounds, the majority of which contain an oxo and/or a sulfonylamino substituent in the spiro cyclic ring system. Of the remainder compounds, the main part has another polar substituent attached to the spiro nucleus and/or they have some polar substituents in the substituent on the piperidine N-atom. No suggestion or indication of effect of the compounds on the sigma receptor is given.

Patent applications EP 518 805 A and WO 02/102387 describe sigma receptor ligands having piperidine or spiropiperidine structures.

With regard to the chemical structure of the compounds described in the present patent application, there are some documents in the prior art which disclose pyrazole derivatives characterized, among other things, for being substituted by amino alkoxy groups in different positions of the pyrazole group.

U.S. Pat. No. 4,337,263 discloses 1-aryl-4-arylsulphonyl-3-amino propoxy-1H-pyrazoles, wherein the amino group can be constituted by an N-cycle group as morpholine, piperidine or pyrrolidine group. They are used as hypolipemiant or hypocholesteroleminant agents.

Patent FR 2301250 describes similar compounds as those mentioned above, such as 1,4-diaryl-3-aminoalkoxy pyrazoles, wherein the amino group comprises pyrrolidine, piperidine, hydroxypiperidine, morpholine or piperazine derivatives.

Patent Application US2003/0144309 refers to pyrazoles with their 3 position substituted by a dimethylaminoethoxy group and present in their 4 position a pyrimidine group. They are used as inhibitors of JNK3, Lck or Src kinase activity.

International patent Application WO 02/092573 describes substituted pyrazole compounds as inhibitors of SRC and other protein kinases.

International patent Application WO 2004/017961 discloses pyrazol compounds wherein the 3 position is substituted by an alkoxy group directly bounded to a cyclic amide, which are used for therapeutically treating and/or preventing a sex hormone related condition in a patient.

U.S. Pat. No. 6,492,529 describes pyrazole derivatives which are used for the treatment of inflammatory diseases. These compounds present in the 5 position a urea group, linked in some cases to a morpholine ethoxy group.

International patent Application WO 04/016592 refers to pyrazole compounds for inhibiting protein prenylation which comprises in the 5 position, among others, an alkoxy group directly bonded to a cyclic amide.

However, none of these documents suggests the effect of these compounds on the sigma receptor.

There is still a need to find compounds that have pharmacological activity towards the sigma receptor, being both effective and selective, and having good "drugability" properties, i.e. good pharmaceutical properties related to administration, distribution, metabolism and excretion.

SUMMARY OF THE INVENTION

We have now found a family of structurally distinct pyrazol derivatives which are particularly selective inhibitors of the sigma receptor. The compounds present a pyrazol group which are characterized by the substitution at position 3 by an alkoxy group directly bounded to a nitrogen.

The invention is directed to a compound of the formula I:

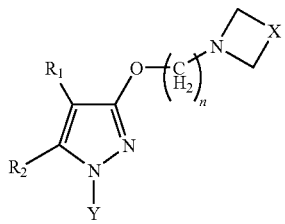

(I)

wherein
R$_1$ is selected from the group formed by hydrogen, substituted or unsubstituted alkyl, substituted or unsubstituted cycloalkyl, substituted or unsubstituted aryl, substituted or unsubstituted alkenyl, substituted or unsubstituted arylalkyl, substituted or unsubstituted heterocyclyl, substituted or unsubstituted heterocyclylalkyl, —COR$_8$, —C(O)OR$_8$, —C(O)NR$_8$R$_9$—C=NR$_8$, —CN, —OR$_8$, —OC(O)R$_8$, —S(O)$_t$—R$_8$, —NR$_8$R$_9$, —NR$_8$C(O)R$_9$, —NO$_2$, —N=CR$_8$R$_9$, or halogen;

R$_2$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —COR$_8$, —C(O)OR$_8$, —C(O)NR$_8$R$_9$—C=NR$_8$, —CN, —OR$_8$, —OC(O)R$_8$, —S(O)$_t$—R$_8$, —NR$_8$R$_9$, —NR$_8$C(O)R$_9$, —NO$_2$, —N=CR$_8$R$_9$, or halogen;

Y is selected from substituted or unsubstituted phenyl or naphtyl; substituted or unsubstituted, branched or linear C$_{1-6}$-alkyl; substituted or unsubstituted C$_{3-8}$-cycloalkyl; substituted or unsubstituted heterocyclyl;

X is selected from:
—CH$_2$—CH$_2$—CH$_2$—CHR$_x$—,
—CH$_2$—CH$_2$—CHR$_x$—, —CH$_2$—,
—CH$_2$-Het-CH$_2$—CHR$_x$—,
—CH$_2$—CH$_2$—CHR$_x$-Het-,
-Het-CH$_2$—CH$_2$—CHR$_x$—,
—CH$_2$—CH$_2$-Het-CHR$_x$—,
CH$_2$-Het-CHR$_x$—,
—CH$_2$—CHR$_x$-Het-,
-Het-CH$_2$—CHR$_x$—,
—CH$_2$—CH$_2$—CHR$_x$—,
—CH$_2$—CHR$_x$—CH$_2$—,
-Het-CHR$_x$—,
—CH$_2$—CHR$_x$—,
with
Het being NH, S or O,
—CHR$_x$— being

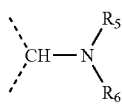

with
R$_5$ and R$_6$, identical or different, represent a hydrogen atom; an optionally substituted C$_{1-4}$ alkyl group; an optionally substituted aryl group; an optionally substituted heteroaryl group; a C$_{1-4}$ alkoxy group; a benzyl group; a phenethyl group;
or
form, together with their bridging nitrogen atom, an optionally substituted heteroaryl group which is optionally condensed to other, optionally at least one heteroatom containing mono- or polycyclic ring system which is optionally at least mono-substituted;
or
X is selected from:
—CH$_2$—CH$_2$—CH$_2$—NR$_x$—,
—CH$_2$—CH$_2$—NR$_x$—CH$_2$—,
—CH$_2$—CH$_2$—CH$_2$—CHR$_x$—,
—CH$_2$—CH$_2$—CHR$_x$—CH$_2$—,
—CH$_2$-Het-CH$_2$—CHR$_x$—,
—CH$_2$—CH$_2$—CHR$_x$-Het-,
-Het-CH$_2$—CH$_2$—CHR$_x$—,
—CH$_2$—CH$_2$-Het-CHR$_x$—,
—CH$_2$-Het-CHR$_x$—,
—CH$_2$—CHR$_x$-Het-,
-Het-CH$_2$—CHR$_x$—,
—CH$_2$—CH$_2$—CHR$_x$—,
—CH$_2$—CHR$_x$—CH$_2$—,
—CH$_2$—CH$_2$—NR$_x$—,
—CH$_2$—NR$_x$—CH$_2$—,
-Het-CHR$_x$—,
—CH$_2$—CHR$_x$—,
—CH$_2$—NR$_x$—,
with
Het being NH, S or O,
R$_x$ being a —(C=O)—R$^{10}$; or a —(C=O)—O—R$^{11}$ group; with
R$^{10}$ and R$^{11}$ independently represent a hydrogen atom; a saturated or unsaturated, optionally at least mono-substituted C$_{1-6}$ alkyl group; an optionally at least mono-substituted aryl group; an optionally at least mono-substituted heteroaryl group; an optionally at least mono-substituted, optionally at least one heteroatom as ring member containing cycloalkyl group; a saturated or unsaturated, optionally at least mono-substituted $C_{1-6}$ alkyl-aryl group; a saturated or unsaturated, optionally at least mono-substituted $C_{1-6}$ alkyl-heteroaryl group; a saturated or unsaturated, optionally at least mono-substituted $C_{1-6}$ alkyl-cycloalkyl group wherein the cycloalkyl group contains optionally at least one heteroatom as ring member;

n is selected from 1, 2, 3, 4, 5, 6, 7 or 8;

t is 1, 2 or 3;

$R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, or halogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment the compound according to the invention is a compound of the formula IB:

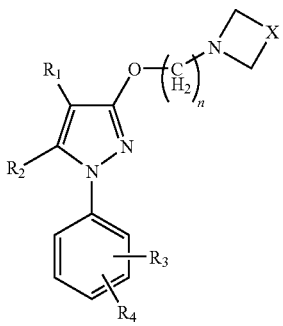

(IB)

wherein $R_1$ is selected from the group formed by hydrogen; substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted aromatic heterocyclyl, substituted or unsubstituted heterocyclyl, substituted or unsubstituted heterocyclylalkyl, —$COR_8$, —$C(O)OR_8$, —$C(O)NR_8R_9$—$C$=$NR_8$, —CN, —$OR_8$, —$OC(O)R_8$, —$NR_8R_9$, —$NR_8C(O)R_9$, —$NO_2$, —N=$CR_8R_9$ or halogen, $R_2$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$—$C$=$NR_8$, —CN, —$OR_8$, —$OC(O)R_8$, —$S(O)_t$—$R_8$, —$NR_8R_9$, —$NR_8C(O)R_9$, —$NO_2$, —N=$CR_8R_9$, or halogen;

$R_3$ and $R_4$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$—$C$=$NR_8$, —CN, —$OR_8$, —$OC(O)R_8$, —$S(O)_t$—$R_8$, —$NR_8R_9$, —$NR_8C(O)R_9$, —$NO_2$, —N=$CR_8R_9$, or halogen, or together they form a fused ring system, X is selected from:
—$CH_2$—$CH_2$—$CH_2$—$CHR_x$—,
—$CH_2$—$CH_2$—$CHR_x$—$CH_2$—,
—$CH_2$-Het-$CH_2$—$CHR_x$—,
—$CH_2$—$CH_2$—$CHR_x$-Het-,
-Het-$CH_2$—$CH_2$—$CHR_x$—,
—$CH_2$—$CH_2$-Het-$CHR_x$—,
—$CH_2$-Het-$CHR_x$—,
—$CH_2$—$CHR_x$-Het-,
-Het-$CH_2$—$CHR_x$—,
—$CH_2$—$CH_2$—$CHR_x$—,
—$CH_2$—$CHR_x$—$CH_2$—,
-Het-$CHR_x$—,
—$CH_2$—$CHR_x$—, with Het being NH, S or O, —$CHR_x$— being

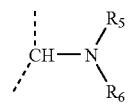

and $R_5$ and $R_6$, identical or different, represent a hydrogen atom; an optionally substituted $C_{1-4}$ alkyl group; an optionally substituted aryl group; an optionally substituted heteroaryl group; a $C_{1-4}$ alkoxy group; a benzyl group; a phenethyl group; or form, together with their bridging nitrogen atom, an optionally substituted heteroaryl group which is optionally condensed to other, optionally at least one heteroatom containing mono- or polycyclic ring system which is optionally at least mono-substituted;

or

X is selected from:
—$CH_2$—$CH_2$—$CH_2$—$NR_x$—,
—$CH_2$—$CH_2$—$NR_x$—$CH_2$—,
—$CH_2$—$CH_2$—$CH_2$—$CHR_x$—,
—$CH_2$—$CH_2$—$CHR_x$—$CH_2$—,
—$CH_2$-Het-$CH_2$—$CHR_x$—,
—$CH_2$—$CH_2$—$CHR_x$-Het-,
-Het-$CH_2$—$CH_2$—$CHR_x$—,
—$CH_2$—$CH_2$-Het-$CHR_x$—,
—$CH_2$-Het-$CHR_x$—,
—$CH_2$—$CHR_x$-Het-,
-Het-$CH_2$—$CHR_x$—,
—$CH_2$—$CH_2$—$CHR_x$—,
—$CH_2$—$CHR_x$—$CH_2$—,
—$CH_2$—$CH_2$—$NR_x$—,
—$CH_2$—$NR_x$—, —$CH_2$—,
-Het-$CHR_x$—,
—$CH_2$—$CHR_x$—,
—$CH_2$—$NR_x$—, with Het being NH, S or O, $R_x$ being a —(C=O)—$R^{10}$; or a —(C=O)—O—$R^{11}$ group; with $R^{10}$ and $R^{11}$ independently represent a hydrogen atom; a saturated or unsaturated, optionally at least mono-substituted $C_{1-6}$ alkyl group; an optionally at least mono-substituted aryl group; an optionally at least mono-substituted heteroaryl group; an optionally at least mono-substituted, optionally at least one heteroatom as ring member containing cycloalkyl group; a saturated or unsaturated, optionally at least mono-substituted $C_{1-6}$ alkyl-aryl group; a saturated or unsaturated, optionally at least mono-substituted $C_{1-6}$ alkyl-heteroaryl group; a saturated or unsaturated, optionally at least mono-substituted $C_{1-6}$ alkyl-cycloalkyl group wherein the cycloalkyl group contains optionally at least one heteroatom as ring member;

n is selected from 1, 2, 3, 4, 5, 6, 7 or 8;

t is 1, 2 or 3;

$R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, or halogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Another preferred embodiment of Group A according to the invention is a compound of the formula I:

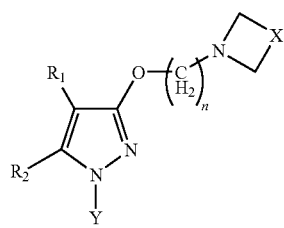

(I)

wherein $R_1$ is selected from the group formed by hydrogen, substituted or unsubstituted alkyl, substituted or unsubstituted cycloalkyl, substituted or unsubstituted aryl, substituted or unsubstituted alkenyl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$—$C$=$NR_8$, —CN, —$OR_8$, —$OC(O)R_8$, —$S(O)_t$—$R_8$, —$NR_8R_9$, —$NR_8C(O)R_9$, —$NO_2$, —N=$CR_8R_9$, or halogen;

$R_2$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$—$C$=$NR_8$, —CN, —$OR_8$, —$OC(O)R_8$, —$S(O)_t$—$R_8$, —$NR_8R_9$, —$NR_8C(O)R_9$, —$NO_2$, —N=$CR_8R_9$, or halogen;

Y is selected from substituted or unsubstituted phenyl or naphtyl; substituted or unsubstituted, branched or linear $C_{1-6}$-alkyl; substituted or unsubstituted $C_{3-8}$-cycloalkyl; substituted or unsubstituted heterocyclyl;

X is selected from:
—$CH_2$—$CH_2$—$CH_2$—$CHR_x$—,
—$CH_2$—$CH_2$—$CHR_x$—$CH_2$—,
—$CH_2$-Het-$CH_2$—$CHR_x$—,
—$CH_2$—$CH_2$—$CHR_x$-Het-,
-Het-$CH_2$—$CH_2$—$CHR_x$—,
—$CH_2$—$CH_2$-Het-$CHR_x$—,
—$CH_2$-Het-$CHR_x$—,
—$CH_2$—$CHR_x$-Het-,
-Het-$CH_2$—$CHR_x$—,
—$CH_2$—$CH_2$—$CHR_x$—,
—$CH_2$—$CHR_x$—$CH_2$—,
-Het-$CHR_x$—,
—$CH_2$—$CHR_x$—,
with
Het being NH, S or O,
—$CHR_x$— being

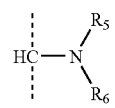

with $R_5$ and $R_6$, identical or different, represent a hydrogen atom; an optionally substituted $C_{1-4}$ alkyl group; an optionally substituted aryl group; an optionally substituted heteroaryl group; a $C_{1-4}$ alkoxy group; a benzyl group; a phenethyl group;

or form, together with their bridging nitrogen atom, an optionally substituted heteroaryl group which is optionally condensed to other, optionally at least one heteroatom containing mono- or polycyclic ring system which is optionally at least mono-substituted;

n is selected from 1, 2, 3, 4, 5, 6, 7 or 8;

t is 1, 2 or 3;

$R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, or halogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Another preferred embodiment of Group A according to the invention is a compound of the formula IB:

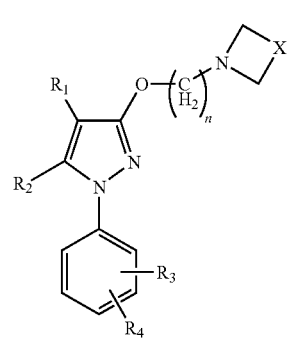

(IB)

wherein
R₁ is selected from the group formed by hydrogen; substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted aromatic heterocyclyl, substituted or unsubstituted heterocyclyl, substituted or unsubstituted heterocyclylalkyl, —COR₈, —C(O)OR₈, —C(O)NR₈R₉—C=NR₈, —CN, —OR₈, —OC(O)R₈, —NR₈R₉, —NR₈C(O)R₉, —NO2, —N=CR₈R₉ or halogen, R₂ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —COR₈, —C(O)OR₈, —C(O)NR₈R₉—C=NR₈, —CN, —OR₈, —OC(O)R₈, —S(O)$_t$—R₈, —NR₈R₉, —NR₈C(O)R₉, —NO₂, —N=CR₈R₉, or halogen;

R₃ and R₄ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —COR₈, —C(O)OR₈, —C(O)NR₈R₉—C=NR₈, —CN, —OR₈, —OC(O)R₈, —S(O)$_t$—R₈, —NR₈R₉, —NR₈C(O)R₉, —NO2, —N=CR₈R₉, or halogen, or together they form a fused ring system, X is selected from:
—CH₂—CH₂—CH₂—CHR$_x$—,
—CH₂—CH₂—CHR$_x$—CH₂—,
—CH₂-Het-CH₂—CHR$_x$—,
—CH₂—CH₂—CHR$_x$-Het-,
-Het-CH₂—CH₂—CHR$_x$—,
—CH₂—CH₂-Het-CHR$_x$—,
—CH₂-Het-CHR$_x$—,
—CH₂—CHR$_x$-Het-,
-Het-CH₂—CHR$_x$—,
—CH₂—CH₂—CHR$_x$—,
—CH₂—CHR$_x$—CH₂—,
-Het-CHR$_x$—,
—CH₂—CHR$_x$—,
with
Het being NH, S or O,
—CHR$_x$— being

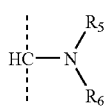

with
R₅ and R₆, identical or different, represent a hydrogen atom; an optionally substituted C₁₋₄ alkyl group; an optionally substituted aryl group; an optionally substituted heteroaryl group; a C₁₋₄ alkoxy group; a benzyl group; a phenethyl group;
or
form, together with their bridging nitrogen atom, an optionally substituted heteroaryl group which is optionally condensed to other, optionally at least one heteroatom containing mono- or polycyclic ring system which is optionally at least mono-substituted;

n is selected from 1, 2, 3, 4, 5, 6, 7 or 8;
t is 1, 2 or 3;
R₈ and R₉ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, or halogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Another preferred embodiment of Group B according to the invention is a compound of the formula I:

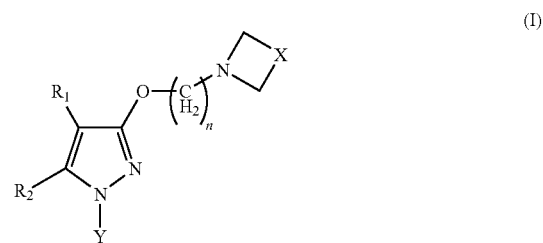

(I)

wherein
R₁ is selected from the group formed by hydrogen, substituted or unsubstituted alkyl, substituted or unsubstituted cycloalkyl, substituted or unsubstituted aryl, substituted or unsubstituted alkenyl, substituted or unsubstituted arylalkyl, substituted or unsubstituted heterocyclyl, substituted or unsubstituted heterocyclylalkyl, —COR₈, —C(O)OR₈, —C(O)NR₈R₉—C=NR₈, —CN, —OR₈, —OC(O)R₈, —S(O)$_t$—R₈, —NR₈R₉, —NR₈C(O)R₉, —NO₂, —N=CR₈R₉, or halogen;

R₂ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —COR₈, —C(O)OR₈, —C(O)NR₈R₉—C=NR₈, —CN, —OR₈, —OC(O)R₈, —S(O)$_t$—R₈, —NR₈R₉, —NR₈C(O)R₉, —NO₂, —N=CR₈R₉, or halogen;

Y is selected from substituted or unsubstituted phenyl or naphtyl; substituted or unsubstituted, branched or linear C₁₋₆-alkyl; substituted or unsubstituted C₃₋₈-cycloalkyl; substituted or unsubstituted heterocyclyl;

X is selected from:
—CH₂—CH₂—CH₂—NR$_x$—,
—CH₂—CH₂—NR$_x$—CH₂—,
—CH₂—CH₂—CH₂—CHR$_x$—,
—CH₂—CH₂—CHR$_x$—CH₂—,
—CH₂-Het-CH₂—CHR$_x$—,
—CH₂—CH₂—CHR$_x$-Het-,
-Het-CH₂—CH₂—CHR$_x$—,
—CH₂—CH₂-Het-CHR$_x$—,
—CH₂-Het-CHR$_x$—,
—CH₂—CHR$_x$-Het-,
-Het-CH₂—CHR$_x$—,
—CH₂—CH₂—CHR$_x$—, —CH$_2$—CHR$_x$—CH$_2$—,
CH$_2$—CH$_2$—NR$_x$—,
—CH$_2$—NR$_x$—CH$_2$—,
-Het-CHR$_x$—,
—CH$_2$—CHR$_x$—,
—CH$_2$—NR$_x$—,
with
Het being NH, S or O,
R$_x$ being a —(C=O)—R$^{10}$; or a —(C=O)—O—R$^{11}$ group;
and
R$^{10}$ and R$^{11}$ independently represent a hydrogen atom; a saturated or unsaturated, optionally at least mono-substituted C$_{1-6}$ alkyl group; an optionally at least mono-substituted aryl group; an optionally at least mono-substituted heteroaryl group; an optionally at least mono-substituted, optionally at least one heteroatom as ring member containing cycloalkyl group; a saturated or unsaturated, optionally at least mono-substituted C$_{1-6}$ alkyl-aryl group; a saturated or unsaturated, optionally at least mono-substituted C$_{1-6}$ alkyl-heteroaryl group; a saturated or unsaturated, optionally at least mono-substituted C$_{1-6}$ alkyl-cycloalkyl group wherein the cycloalkyl group contains optionally at least one heteroatom as ring member;
n is selected from 1, 2, 3, 4, 5, 6, 7 or 8;
t is 1, 2 or 3;
R$_8$ and R$_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, or halogen;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Another preferred embodiment of Group A according to the invention is a compound of the formula IB:

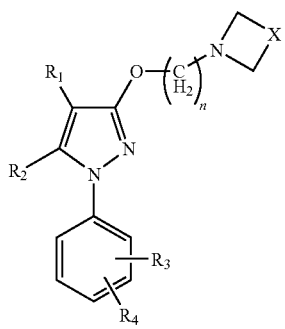

(IB)

wherein
R$_1$ is selected from the group formed by hydrogen; substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted aromatic heterocyclyl, substituted or unsubstituted heterocyclyl, substituted or unsubstituted heterocyclylalkyl, —COR$_8$, —C(O)OR$_8$, —C(O)NR$_8$R$_9$—C=NR$_8$, —CN, —OR$_8$, —OC(O)R$_8$, —NR$_8$R$_9$, —NR$_8$C(O)R$_9$, —NO2, —N=CR$_8$R$_9$ or halogen,
R$_2$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —COR$_8$, —C(O)OR$_8$, —C(O)NR$_8$R$_9$—C=NR$_8$, —CN, —OR$_8$, —OC(O)R$_8$, —S(O)$_t$—R$_8$, —NR$_8$R$_9$, —NR$_8$C(O)R$_9$, —NO$_2$, —N=CR$_8$R$_9$, or halogen;
R$_3$ and R$_4$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —COR$_8$, —C(O)OR$_8$, —C(O)NR$_8$R$_9$—C=NR$_8$, —CN, —OR$_8$, —OC(O)R$_8$, —S(O)$_t$ —R$_8$, —NR$_8$R$_9$, —NR$_8$C(O)R$_9$, —NO$_2$, —N=CR$_8$R$_9$, or halogen, or together they form a fused ring system,
X is selected from:
—CH$_2$—CH$_2$—CH$_2$—NR$_x$—,
—CH$_2$—CH$_2$—NR$_x$, —CH$_2$—,
—CH$_2$—CH$_2$—CH$_2$—CHR$_x$—,
—CH$_2$—CH$_2$—CHR$_x$—CH$_2$—,
—CH$_2$-Het-CH$_2$—CHR$_x$—,
—CH$_2$—CH$_2$—CHR$_x$-Het-,
-Het-CH$_2$—CH$_2$—CHR$_x$—,
—CH$_2$—CH$_2$-Het-CHR$_x$—,
—CH$_2$-Het-CHR$_x$—,
—CH$_2$—CHR$_x$-Het-,
-Het-CH$_2$—CHR$_x$—,
—CH$_2$—CH$_2$—CHR$_x$—,
—CH$_2$—CHR$_x$—CH$_2$—,
—CH$_2$—CH$_2$—NR$_x$—,
—CH$_2$—NR$_x$—CH$_2$—,
-Het-CHR$_x$—,
—CH$_2$—CHR$_x$—,
—CH$_2$—NR$_x$—,
with
Het being NH, S or O,
R$_x$ being a —(C=O)—R$^{10}$; or a —(C=O)—O—R$^{11}$ group;
and
R$^{10}$ and R$^{11}$ independently represent a hydrogen atom; a saturated or unsaturated, optionally at least mono-substituted C$_{1-6}$ alkyl group; an optionally at least mono-substituted aryl group; an optionally at least mono-substituted heteroaryl group; an optionally at least mono-substituted, optionally at least one heteroatom as ring member containing cycloalkyl group; a saturated or unsaturated, optionally at least mono-substituted C$_{1-6}$ alkyl-aryl group; a saturated or unsaturated, optionally at least mono-substituted C$_{1-6}$ alkyl-heteroaryl group; a saturated or unsaturated, optionally at least mono-substituted C$_{1-6}$ alkyl-cycloalkyl group wherein the cycloalkyl group contains optionally at least one heteroatom as ring member;
n is selected from 1, 2, 3, 4, 5, 6, 7 or 8;
t is 1, 2 or 3;
R$_8$ and R$_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, or halogen;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In one embodiment $R_1$ of formulas I or IB is selected from H, halogen, —$COR_8$, or substituted or unsubstituted alkyl, preferably it is selected from H, Cl, methyl or acetyl.

In one embodiment $R_1$ of formulas I or IB is hydrogen.

In one embodiment $R_2$ of formulas I or IB is H, aryl, $C(O)OR_8$ or alkyl, preferably methyl, iso-propyl, phenyl, $C(O)O$—$C_2H_5$ or H.

In one embodiment $R_3$ and $R_4$ of formula IB are situated in the meta and para positions of the phenyl group.

In one embodiment $R_3$ and $R_4$ of formula IB are independently selected from halogen, hydrogen, alkoxy, or substituted or unsubstituted alkyl, more preferably selected from hydrogen, halogen, Cl, methoxy or haloalkyl.

In one embodiment $R_3$ and $R_4$ of formula IB together form a fused ring system, especially a fused ring system leading with the phenyl to form a naphthyl-radical.

In one embodiment n of formula I or IB is selected from 2, 3, 4.

In one embodiment of Group A X of formulas I or IB is selected from

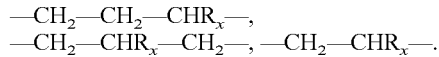

In one embodiment of Group A $R_5$ and $R_6$ of formula I or IB are selected from hydrogen or alkyl or
form, together with their bridging nitrogen atom, an optionally substituted heteroaryl group which is optionally condensed to other, optionally at least one heteroatom containing mono- or polycyclic ring system which is optionally at least mono-substituted, especially an indazole or an 1H-indazole.

In one embodiment of Group A the compound is selected from
3-{1-[2-(1-(3,4-Dichlorophenyl)-5-methyl-1H-pyrazol-3-yloxy)ethyl]piperidin-4-yl}-3H-imidazo[4,5-b]pyridine,
3-{1-[2-(1-(3,4-Dichlorophenyl)-5-methyl-1H-pyrazol-3-yloxy)ethyl]piperidin-4-yl}-3H-imidazo[4,5-b]pyridine oxalate,
1-{2-[1-(3,4-Dichlorophenyl)-5-methyl-1H-pyrazol-3-yloxy]ethyl}pyrrolidin-3-amine,
1-{2-[1-(3,4-Dichlorophenyl)-5-methyl-1H-pyrazol-3-yloxy]ethyl}pyrrolidin-3-amine oxalate,
optionally in form of one of the stereoisomers, preferably enantiomers or diastereomers, a racemate or in form of a mixture of at least two of the stereoisomers, preferably enantiomers and/or diastereomers, in any mixing ratio, or another corresponding salt thereof, or a corresponding solvate thereof.

In one embodiment of Group B X of formulas I or IB is selected from

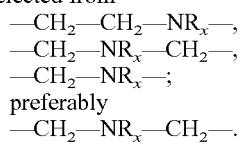

preferably
—$CH_2$—$NR_x$—$CH_2$—.

In one embodiment of Group B $R_{10}$ and $R_{11}$ of formulas I or IB are independently selected from hydrogen or alkyl.

In one embodiment of Group B the compound is selected from
1-{2-[1-(3,4-Dichlorophenyl)-5-methyl-1H-pyrazol-3-yloxy]ethyl}pyrrolidin-3-amine,
1-{2-[1-(3,4-Dichlorophenyl)-5-methyl-1H-pyrazol-3-yloxy]ethyl}pyrrolidin-3-amine oxalate,
1-(4-(2-(1-(3,4-dichlorophenyl)-5-methyl-1H-pyrazol-3-yloxy)ethyl)piperazin-1-yl)ethanone,
1-(4-(2-(1-(3,4-dichlorophenyl)-5-methyl-1H-pyrazol-3-yloxy)ethyl)piperazin-1-yl)ethanone oxalate,
1-{1-[2-(1-(3,4-Dichlorophenyl)-1H-pyrazol-3-yloxy)ethyl]piperidin-4-yl}ethanone,
1-{1-[2-(1-(3,4-Dichlorophenyl)-1H-pyrazol-3-yloxy)ethyl]piperidin-4-yl}ethanone oxalate,
1-{4-[2-(1-(3,4-Dichlo-rophenyl)-1H-pyrazol-3-yloxy)ethyl]pipera-zin-1-yl}ethanone,
1-{4-[2-(1-(3,4-Dichlo-rophenyl)-1H-pyrazol-3-yloxy)ethyl]pipera-zin-1-yl}ethanone oxalate
1-(1-[2-{1-(2,4-Dichlo-rophenyl)-1H-pyrazol-3-yloxy}ethyl]piperi-din-4-yl)ethanone,
1-(1-[2-{1-(2,4-Dichlo-rophenyl)-1H-pyrazol-3-yloxy}ethyl]piperi-din-4-yl)ethanone oxalate,
1-(1-(2-(1-(4-Chloro-phenyl)-1H-pyrazol-3-yloxy)ethyl)piperidin-4-yl)ethanone,
1-(1-(2-(1-(4-Chloro-phenyl)-1H-pyrazol-3-yloxy)ethyl)piperidin-4-yl)ethanone oxalate,
1-(1-(2-(1-(3,4-Dichlo-rophenyl)-5-methyl-1H-pyrazol-3-yloxy)ethyl)piperidin-4-yl)ethanone,
1-(1-(2-(1-(3,4-Dichlo-rophenyl)-5-methyl-1H-pyrazol-3-yloxy)ethyl)piperidin-4-yl)ethanone oxalate,
1-(4-(4-(1-(3,4-Dichlo-rophenyl)-4,5-dimethyl-1H-pyrazol-3-yloxy)butyl)piperazin-1-yl)ethanone,
1-(4-(4-(1-(3,4-Dichlo-rophenyl)-4,5-dimethyl-1H-pyrazol-3-yloxy)butyl)piperazin-1-yl)ethanone oxalate,
1-(4-(2-(1-(2,4-Dichlo-rophenyl)-1H-pyrazol-3-yloxy)ethyl)piperazin-1-yl)ethanone,
1-(4-(2-(1-(2,4-Dichlo-rophenyl)-1H-pyrazol-3-yloxy)ethyl)piperazin-1-yl)ethanone oxalate;
1-(4-(2-(1-(3,4-Dichlo-rophenyl)-4,5-dimethyl-1H-pyrazol-3-yloxy)ethyl)piperazin-1-yl)ethanone,
1-(4-(2-(1-(3,4-Dichlo-rophenyl)-4,5-dimethyl-1H-pyrazol-3-yloxy)ethyl)piperazin-1-yl)ethanone oxalate,
1-(4-{4-[1-(3,4-Dichloro-phenyl)-5-methyl-1H-pyrazol-3-yloxy]-butyl}-piperazin-1-yl)-ethanone
1-(4-{4-[1-(3,4-Dichloro-phenyl)-5-methyl-1H-pyrazol-3-yloxy]-butyl}-piperazin-1-yl)-ethanone oxalate;
optionally in form of one of the stereoisomers, preferably enantiomers or diastereomers, a racemate or in form of a mixture of at least two of the stereoisomers, preferably enantiomers and/or diastereomers, in any mixing ratio, or another corresponding salt thereof, or a corresponding solvate thereof.

Another aspect the invention is directed to a process for the preparation of a compound of formula (I) or a salt, isomer or solvate thereof.

In another aspect the invention is directed to a pharmaceutical composition which comprises a compound as above defined or a pharmaceutically acceptable salt, enantiomer, prodrug or solvate thereof, and a pharmaceutically acceptable carrier, adjuvant or vehicle.

In a further aspect the invention is directed to the use of a compound of formula I or IB for the treatment or prophylaxis of a sigma receptor mediated disease or condition.

In another preferred embodiment the compounds as above defined are used in the manufacture of a medicament for the treatment of diarrhea, lipoprotein disorders, metabolic syndrome, treatment of elevated triglyceride levels, chylomicronemia, hyperlipoproteinemia; hyperlipidemia, especially mixed hyperlipidemia; hypercholesterolemia, dysbetalipoproteinemia, hypertriglyceridemia including both the sporadic and familial disorder (inherited hypertriglyceridemia), migraine, obesity, arthritis, hypertension, arrhythmia, ulcer, learning, memory and attention deficits, cognition disorders, neurodegenerative diseases, demyelinating diseases, addiction to drugs and chemical substances including cocaine, amphetamine, ethanol and nicotine, tardive diskinesia, ischemic stroke, epilepsy, stroke, depression, stress, psychotic condition, schizophrenia; inflammation, autoimmune diseases or cancer; disorders of food ingestion, the regulation of appetite, for the reduction, increase or maintenance of body weight, for the prophylaxis and/or treatment of obesity, bulimia, anorexia, cachexia or type II diabetes, preferably type II diabetes caused by obesity; or to the use as pharmacological tool, as anxiolytic or as immunosuppressant.

In a more preferred embodiment the medicament is for the treatment of pain, especially neuropathic pain, inflammatory pain or other pain conditions, allodynia and/or hyperalgesia, especially mechanical allodynia.

The above mentioned preferences and embodiments can be combined to give further preferred compounds or uses.

DETAILED DESCRIPTION OF THE INVENTION

The typical compounds of this invention effectively and selectively inhibit the sigma receptor.

In the present description the following terms have the meaning indicated:

"Alkyl" refers to a straight or branched hydrocarbon chain radical consisting of carbon and hydrogen atoms, containing no saturation, having one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as a aryl, halo, hydroxy, alkoxy, carboxy, cyano, carbonyl, acyl, alkoxycarbonyl, amino, nitro, mercapto, alkylthio, etc. If substituted by aryl we have an "Aralkyl" radical, such as benzyl and phenethyl.

"Alkenyl" refers to an alkyl radical having at least 2 C atoms and having one or more unsaturated bonds.

"Cycloalkyl" refers to a stable 3- to 10-membered monocyclic or bicyclic radical which is saturated or partially saturated, and which consist solely of carbon and hydrogen atoms, such as cyclohexyl or adamantyl. Unless otherwise stated specifically in the specification, the term "cycloalkyl" is meant to include cycloalkyl radicals which are optionally substituted by one or more substituents such as alkyl, halo, hydroxy, amino, cyano, nitro, alkoxy, carboxy, alkoxycarbonyl, etc.

"Aryl" refers to single and multiple ring radicals, including multiple ring radicals that contain separate and/or fused aryl groups. Typical aryl groups contain from 1 to 3 separated or fused rings and from 6 to about 18 carbon ring atoms, such as phenyl, naphthyl, indenyl, fenanthryl or anthracyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

"Heterocyclyl" refers to a stable 3- to 15 membered ring radical which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. It may be aromatic or not aromatic. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran, coumarine, morpholine; pyrrole, pyrazole, oxazole, isoxazole, triazole, imidazole, etc. "Heterocyclylalkyl" refers accordingly to a "Heterocyclyl" radical being connected via an "Alkyl" chain.

"Alkoxy" refers to a radical of the formula —ORa where Ra is an alkyl radical as defined above, e.g., methoxy, ethoxy, propoxy, etc.

"Amino" refers to a radical of the formula —NH2, —NHRa or —NRaRb, optionally quaternized.

"Halo" or "hal" refers to halogen such as bromo, chloro, iodo or fluoro.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; amino, azido; esters, e.g. esters of carbonic acid etc.; (C=O) groups such as e.g. acetyl, propanoyl etc.; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

In a preferred embodiment particular individual compounds listed below and falling under formula (I) are excluded/disclaimed from the invention:

Ex1: 3-{1-[2-(1-(3,4-Dichlorophenyl)-5-methyl-1H-pyrazol-3-yloxy)ethyl]piperidin-4-yl}-3H-imidazo[4,5-b]pyridine;

Ex2: 1-{2-[1-(3,4-Dichlorophenyl)-5-methyl-1H-pyrazol-3-yloxy]ethyl}pyrrolidin-3-amine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon or $^{15}N$-enriched nitrogen are within the scope of this invention.

The term "pharmaceutically acceptable salts, solvates, prodrugs" refers to any pharmaceutically acceptable salt, ester, solvate, or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glucamine and basic aminoacids salts.

Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Any compound that is a prodrug of a compound of formula (I) or (IB) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

The compounds of the invention may be in crystalline form either as free compounds or as solvates and it is intended that both forms are within the scope of the present invention. Methods of solvation are generally known within the art.

Suitable solvates are pharmaceutically acceptable solvates. In a particular embodiment the solvate is a hydrate.

The compounds of formula (I) or (IB) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I) or (IB), or of its salts, solvates or prodrugs.

The compounds of the present invention represented by the above described formula (I) or (IB) may include enantiomers depending on the presence of chiral centres or isomers depending on the presence of multiple bonds (e.g. Z, E). The single isomers, enantiomers or diastereoisomers and mixtures thereof fall within the scope of the present invention.

The compounds of formula (I) or (IB) defined above can be obtained by available synthetic procedures similar to those described in the U.S. Pat. No. 4,337,263 or FR 2 472 564. For example, they can be prepared by condensing a compound of Formula (II):

in which $R_1$, $R_2$ and Y are as defined above in claim 1, with a compound of Formula (III):

in which X and n are as defined in claims 1 or 2.

The reaction of compounds of formulas (II) and (III) is preferably carried out at a temperature in the range of 60 to 120° C. in an aprotic solvent, but not limited to, such as dimethylformamide (DMF) in the presence of an inorganic base, such as $K_2CO_3$.

A general scheme for synthesizing compounds (II), (I) or (IB) is:

General Scheme of Synthesis

Scheme I:

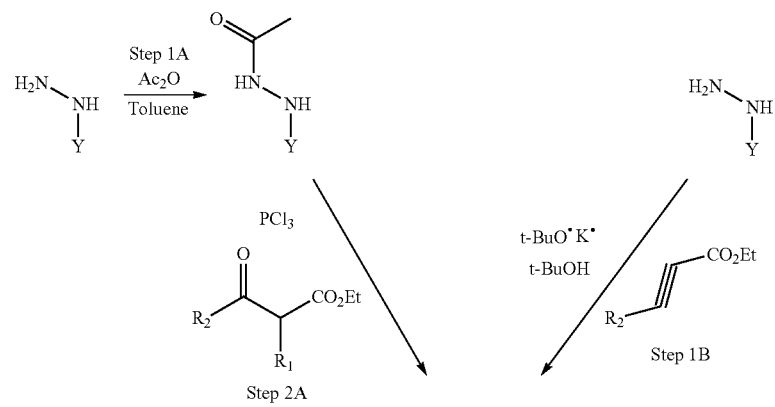

-continued
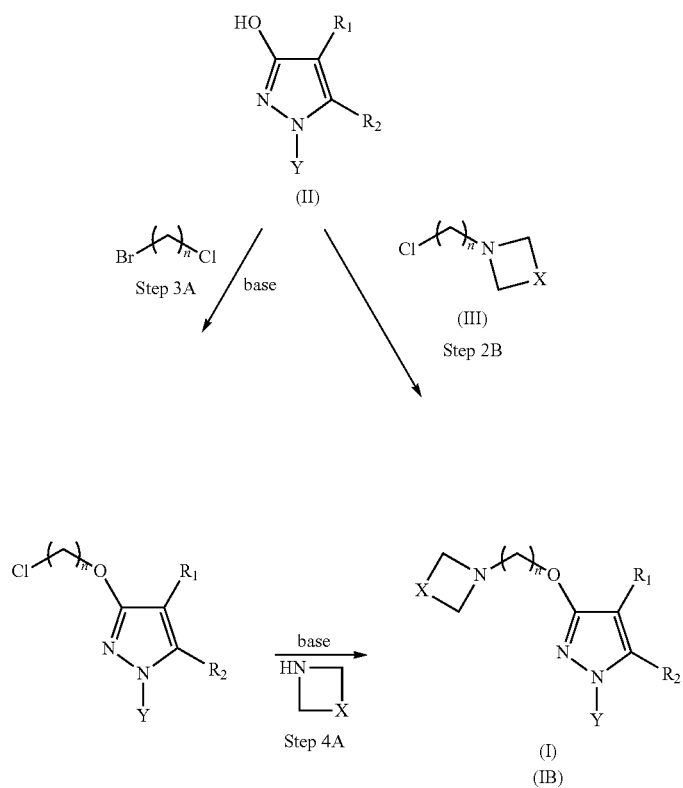
Scheme II
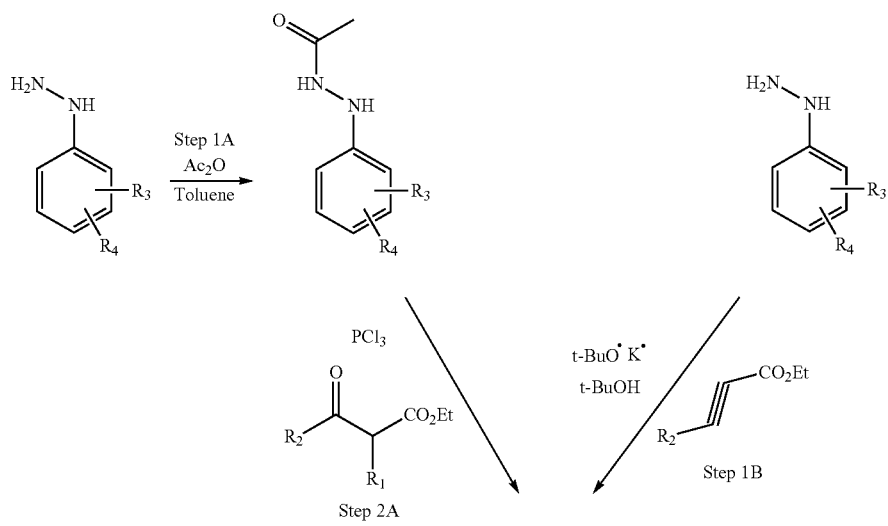

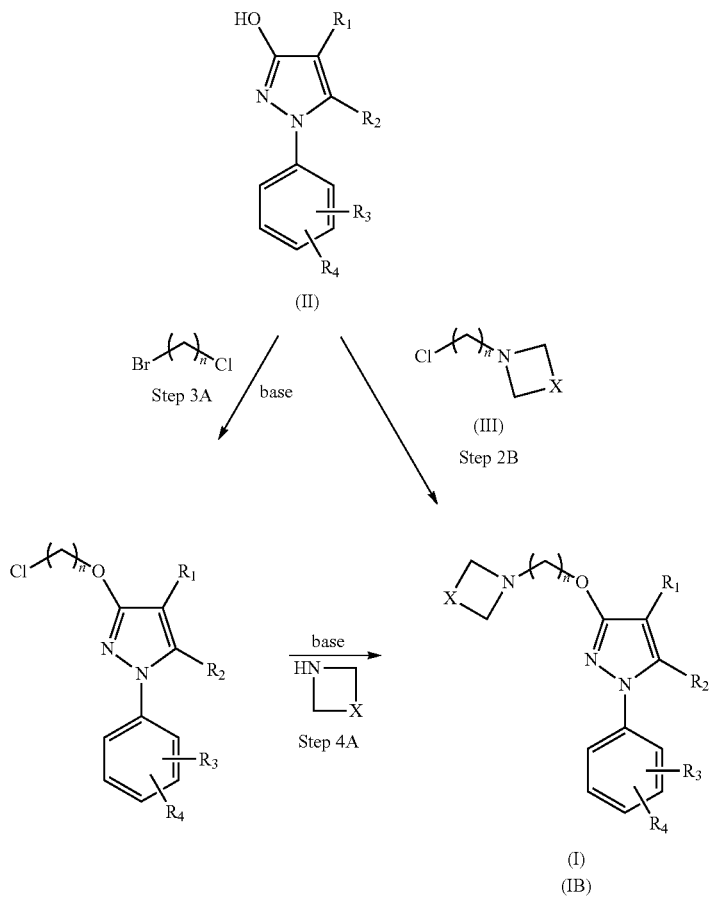

The intermediate compound (II) can also be prepared as described in the bibliography (see L. F. Tietze et al., Synthesis, (11), 1079-1080, 1993; F. Effenberger and W. Hartmann, Chem. Ber., 102(10), 3260-3267, 1969; both cites incorporated here by reference). It can also be prepared by conventional methods, as can be seen in the synthetic examples of the present patent application.

Compounds of Formula (III) are commercially available or can be prepared by conventional methods.

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form is the crystalline form, including such form in pharmaceutical composition. In the case of salts and solvates the additional ionic and solvent moieties must also be non-toxic. The compounds of the invention may present different polymorphic forms, it is intended that the invention encompasses all such forms.

Another aspect of this invention relates to a method of treating or preventing a sigma receptor mediated disease which method comprises administering to a patient in need of such a treatment a therapeutically effective amount of a compound as above defined or a pharmaceutical composition thereof. Among the sigma mediated diseases that can be treated are diarrhea, lipoprotein disorders, metabolic syndrome, treatment of elevated triglyceride levels, chylomicronemia, hyperlipoproteinemia; hyperlipidemia, especially mixed hyperlipidemia; hypercholesterolemia, dysbetalipoproteinemia, hypertriglyceridemia including both the sporadic and familial disorder (inherited hypertriglyceridemia), migraine, obesity, arthritis, hypertension, arrhythmia, ulcer, learning, memory and attention deficits, cognition disorders, neurodegenerative diseases, demyelinating diseases, addiction to drugs and chemical substances including cocaine, amphetamine, ethanol and nicotine, tardive diskinesia, ischemic stroke, epilepsy, stroke, depression, stress, pain, especially neuropathic pain, inflammatory pain or other pain conditions, allodynia and/or hyperalgesia, especially mechanical allodynia, psychotic condition, schizophrenia; inflammation, autoimmune diseases or cancer; disorders of food ingestion, the regulation of appetite, for the reduction, increase or maintenance of body weight, for the prophylaxis and/or treatment of obesity, bulimia, anorexia, cachexia or type II diabetes, preferably type II diabetes caused by obesity. The compounds of the invention can also be employed as pharmacological tool or as anxiolytic or immunosuppressant.

The term "pharmacological tool" refers to the property of compounds of the invention through which they are particularly selective ligands for Sigma receptors which implies that compound of formula I, described in this invention, can be used as a model for testing other compounds as Sigma ligands, ex. a radioactive ligands being replaced, and can also be used for modeling physiological actions related to Sigma receptors.

The present invention further provides pharmaceutical compositions comprising a compound of this invention, or a pharmaceutically acceptable salt, derivative, prodrug or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

The following examples are given only as further illustration even if no longer part of the invention.

EXAMPLES

Example 1

Synthesis of 3-{1-[2-(1-(3,4-Dichlorophenyl)-5-methyl-1H-pyrazol-3-yloxy)ethyl]piperidin-4-yl}-3H-imidazo[4,5-b]pyridine Step 1A: Synthesis of Acetic Acid N'-(3,4-Dichlorophenyl)hydrazide (V)

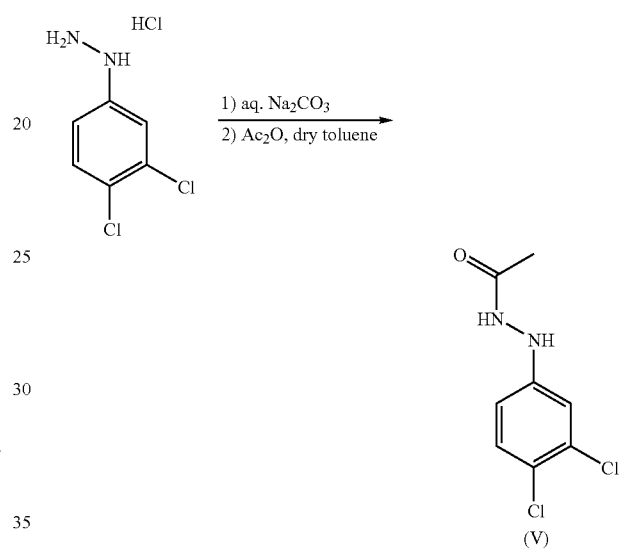

N'-(3,4-Dichlorophenyl)hydrazine was liberated from its hydrochloride (10.0 g, 46.8 mmol) by partitioning the solid between diluted $Na_2CO_3$ solution (10 ml saturated solution and 40 ml water) and AcOEt. The aqueous layer was extracted two more times with AcOEt, the organic extracts were dried ($Na_2SO_4$), the solvent was removed in vacuo, and the residue was taken up in dry toluene (100 ml). To this solution acetic anhydride (4.78 g, 46.8 mmol) was slowly added, and the reaction mixture was stirred at room temperature for 15 min. Light petroleum (50 ml) was added, the mixture was cooled in the refrigerator (−20° C.), and the resulting crystals were collected on a sintered glass funnel and washed with cold petrol ether. Recrystallization from MeOH yielded (V) (8.30 g, 81%) as shiny white crystals, mp 179-182° C. (lit. 168-171° C.). TLC $CHCl_3$/MeOH 9:1.

MS m/z (%): 222/220/218 (W, 3/22/34), 178 (64), 176 (100), 160 (20), 43 (94).

Only the NMR signals of the dominant isomer are given (ratio ca. 9:1):

$^1$H-NMR (DMSO-$d_6$): (ppm) 9.69 (d, 11-1, NH—CO, $^3J$=2.0 Hz), 8.09 (d, 1H, Ph-NH, $^3J$=2.0 Hz), 7.32 (d, 1H, Ph 1-1-5, $^3J$(H5, 1-16)=8.8 Hz), 6.83 (d, 1H, Ph H-2, $^4J$(H2, H6)=2.5 Hz), 6.66 (dd, 1H, Ph H-6, $^4$3(H2, 146) 2.5 Hz, $^3J$(H5, H6)=8.8 Hz), 1.90 (s, 31-1, Me).

$^{13}$C-NMR (DMSO-$d_6$): S (ppm) 169.2 (C=O), 149.6 (Ph C-1), 131.2 (Ph C-3), 130.5 (Ph C-5), 119.1 (Ph C-4), 112.9 (Ph C-2*), 112.4 (Ph C-6*), 20.6 (Me).

Step 2A: Synthesis of 1-(3,4-Dichlorophenyl)-5-methyl-1H-pyrazol-3-ol (VI)

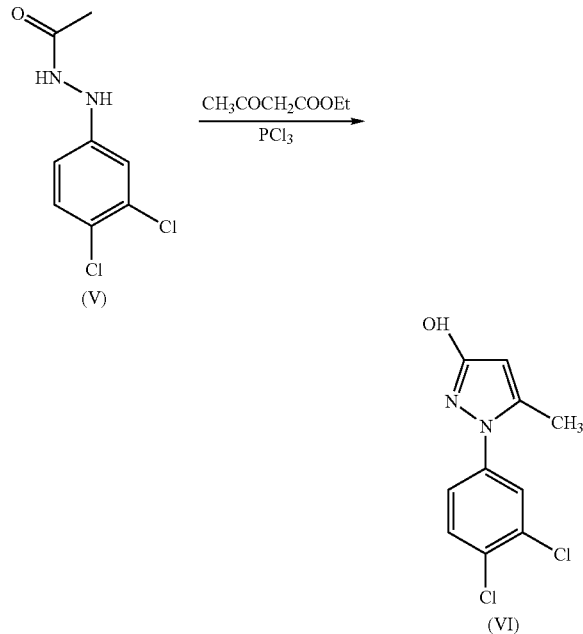

To a mixture of (V) (5.0 g, 22.8 mmol) and ethyl acetoacetate (2.97 g 22.8 mmol) was slowly added $PCl_3$ (3.13 g, 22.8 mmol). The mixture was warmed to 50° C. for 1.5 h, poured into ice water (150 ml), and the resulting precipitate was collected on a sintered glass funnel and recrystallized from EtOH to yield (VI) (2.29 g, 41%) as white crystals, mp 208-211° C. (lit. 208-209° C.), TLC $CHCl_3$/MeOH 9:1.

MS m/z (%): 246/244/242 (M+, 11/59/100), 207 (32), 147 (20), 145 (34), 111 (20), 109 (23), 75 (20).

$^1$H-NMR (CDCl3): S (ppm) 11.72 (broad s, 1H, OH), 7.54 (d, 1H, Ph H-5, 3J(H5, H6)=8.5 Hz), 7.48 (d, 1H, Ph 11-2, 4J(H2, H6)-2.5 Hz), 7.26 (dd, 1H, Ph H-6, 4J(H2, H6)=2.5 Hz, 3J(H5, H6)=83 Hz), 5.63 (s, 1H, 4-H), 2.28 (s, 3H, 5-Me).

$^{13}$C-NMR (CDCl$_3$): 6 (ppm) 163.1 (Pz C-3), 141.2 (Pz C-5), 137.9 (Ph C-1), 133.1 (Ph C-3), 131.4 (Ph C-4), 131.0 (Ph C-5), 126.1 (Ph C-2), 123.6 (Ph C-6), 94.5 (Pz C-4), 12.7 (5-Me).

Step 3A. Synthesis of 3-(2-chloroethoxy)-1-(3,4-dichlorophenyl)-5-methyl-1H-pyrazole

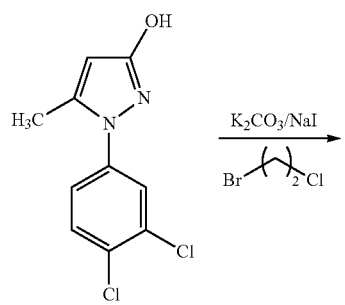

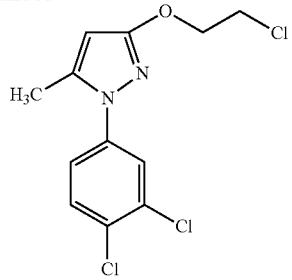

A mixture of 1-(3,4-dichlorophenyl)-5-methyl-1H-pyrazol-3-ol (0.29 g, 1.19 mmol), 1-bromo-2-chloroethane (0.2 μl, 2.4 mmol), $K_2CO_3$ (0.49 g, 3.6 mmol) and NaI (0.18 g, 1.19 mmol) in dry dimethylformamide (25 ml) was stirred overnight at room temperature. Solvent was evaporated in vacuo and the crude residue was partitioned between water/dichloromethane. The organic extracts were washed with water, dried on $Na_2SO_4$ and concentrated in vacuo to obtain 0.33 g of an oily compound, corresponding to a mixture of 3-(2-chloroethoxy)-1-(3,4-dichlorophenyl)-5-methyl-1H-pyrazole, and starting material. Hexane was added to the mixture and stirred for 10 min., the unsoluble material, corresponding to unreacted starting compound, was filtered off, and filtrate evaporated to dryness yielding 0.19 g of 3-(2-chloroethoxy)-1-(3,4-dichlorophenyl)-5-methyl-1H-pyrazole.

$^1$H-NMR (CDCl$_3$) δ ppm: 7.55 (d, J=2.5 Hz, 1H), 7.5 (d, J=8.7 Hz, 1H), 7.3 (dd, J=2.5 and 8.7 Hz, 1H), 5.7 (s, 1H), 4.45 (t, J=5.9 Hz, 2H), 3.8 (t, J=5.9 Hz, 2H), 2.3 (s, 3H).

Step 4A. Synthesis of 3-{1-[2-(1-(3,4-Dichlorophenyl)-5-methyl-1H-pyrazol-3-yloxy)ethyl]piperidin-4-yl}-3H-imidazo[4,5-b]pyridine

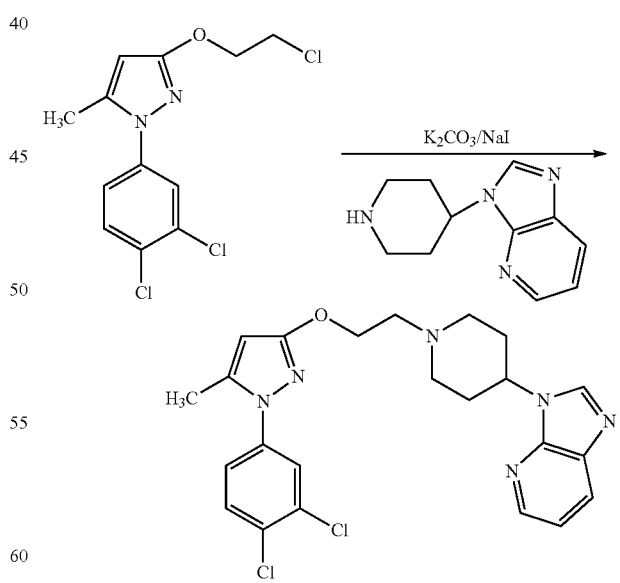

3-(2-chloroethoxy)-1-(3,4-dichlorophenyl)-5-methyl-1H-pyrazole (0.2 g, 0.65 mmol), 3-(piperidin-4-yl)-3H-imidazo[4,5-b]pyridine (0.145 g, 0.72 mmol), $K_2CO_3$ (270 mg, 1.96 mmol) and NaI (98 mg, 0.65 mmol) in dry dimethylformamide (6 ml) was warmed overnight at 85° C., and then an additionally 16 hrs at 95° C., in a dry nitrogen atmosphere. Solvents were evaporated in vacuo and the crude residue partitioned in water/ethyl acetate. The combined organic extracts were washed with water, dried on Na₂SO₄ and concentrated in vacuo to obtain a yellow crude oil, which was purified by column chromatography on silica gel (eluent: ethyl acetate 100% and ethyl acetate/MeOH 98/2 and 95/5) yielding 134 mg of 3-{1-[2-(1-(3,4-Dichlorophenyl)-5-methyl-1H-pyrazol-3-yloxy)ethyl]piperidin-4-yl}-3H-imidazo[4,5-b]pyridine as a white solid with m.p.=104-107° C.

¹H-NMR (CDCl₃) δ ppm: 8.4 (dd, J=1.3 and 4.8 Hz, 1H), 8.2 (s, 1H), 8.1 (dd, J=1.3 and 8.1 Hz, 1H), 7.55 (d, J=2.5 Hz, 1H), 7.5 (d, J=8.7 Hz, 1H), 7.3-7.2 (m+solvent, 2H), 5.7 (s, 1H), 4.75-4.5 (m, 3H), 3.5-3.0 (m, 4H), 2.9-2.4 (m, 2H), 2.3 (m+s, 5H), 1.6 (m, 2H).

Example 2

Synthesis of 1-{2-[1-(3,4-Dichlorophenyl)-5-methyl-1H-pyrazol-3-yloxy]ethyl}pyrrolidin-3-amine Step 1. Synthesis of N-(1-(2-(1-(3,4-dichlorophenyl)-5-methyl-1H-pyrazol-3-yloxy)ethyl)pyrrolidin-3-yl)acetamide

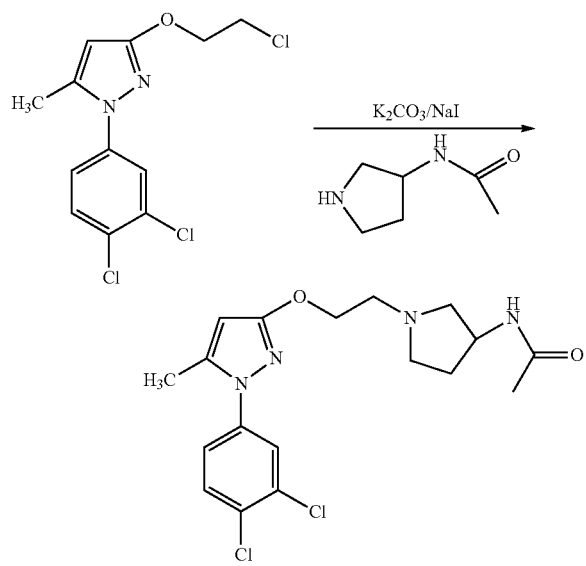

3-(2-chloroethoxy)-1-(3,4-dichlorophenyl)-5-methyl-1H-pyrazole (0.5 g, 1.64 mmol), N-(pyrrolidin-3-yl)acetamide (0.23 g, 1.8 mmol), K₂CO₃ (0.68 g, 4.9 mmol) and NaI (245 mg, 1.64 mmol) in dry dimethylformamide (10 ml) was warmed overnight at 85° C., and then an additionally 16 hrs at 95° C., in a dry nitrogen atmosphere. Solvents were evaporated in vacuo and the crude residue partitioned in water/ethyl acetate. The combined organic extracts were washed with water, dried on Na₂SO₄ and concentrated in vacuo to obtain a yellow crude oil, which was purified by column chromatography on silica gel (eluent: ethyl acetate 100% and ethyl acetate/MeOH 9/1) yielding 192 mg of N-(1-(2-(1-(3,4-dichlorophenyl)-5-methyl-1H-pyrazol-3-yloxy)ethyl)pyrrolidin-3-yl)acetamide as an oil.

¹H-NMR (DMSO-d₆) δ ppm: 7.55 (d, J=2.5 Hz, 1H), 7.5 (d, J=8.6 Hz, 1H), 7.3 (dd, J=2.5 and 8.6 Hz, 1H), 5.7 (s, 1H), 4.45 (t, J=5.2 Hz, 2H), 3.1 (m, 3H), 2.75 (m, 2H), 2.55 (m, 2H), 2.3 (s, 3H), 1.95 (s, 3H), 1.85 (m, 2H).

Step 2. Synthesis of 1-{2-[1-(3,4-Dichlorophenyl)-5-methyl-1H-pyrazol-3-yloxy]ethyl}pyrrolidin-3-amine

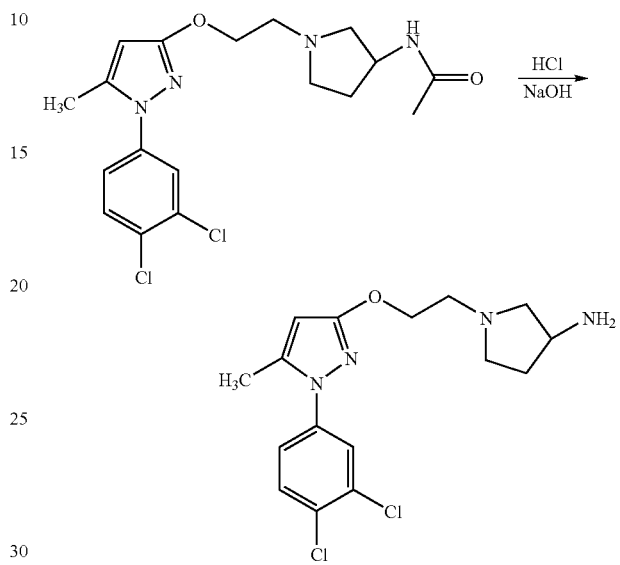

A solution of N-(1-(2-(1-(3,4-dichlorophenyl)-5-methyl-1H-pyrazol-3-yloxy)ethyl)pyrrolidin-3-yl)acetamide (0.1 g, 0.25 mmol) in water (2 ml) and 6N aqueous solution of HCl (2 ml) was refluxed for 5 hrs. The mixture was basified with 20% aqueous solution of NaOH and extracted with dichloromethane. The combined organic solutions was washed with water, dried over Na₂SO₄, filtered and evaporated to dryness yielding 80 mg of 1-{2-[1-(3,4-Dichlorophenyl)-5-methyl-1H-pyrazol-3-yloxy]ethyl}pyrrolidin-3-amine as an oil ¹H-NMR (DMSO-d₆) δ ppm: 7.75 (d, J=2.5 Hz, 1H), 7.7 (d, J=8.7 Hz, 1H), 7.5 (dd, J=2.5 and 8.7 Hz, 1H), 5.8 (s, 1H), 4.15 (t, J=5.7 Hz, 2H), 2.7 (t, J=5.7 Hz, 2H), 2.65-2.5 (m, 4H), 2.3 (s, 3H), 2.2 (m, 1H), 1.95 (m, 1H), 1.35 (m, 1H).

Example 3

Synthesis of Ethyl 4-{2-[1-(3,4-dichlorophenyl)-5-methyl-1H-pyrazol-3-yloxy]ethyl}piperazine carboxylate Step 1A: Synthesis of Acetic Acid N'-(3,4-Dichlorophenyl)hydrazide (V)

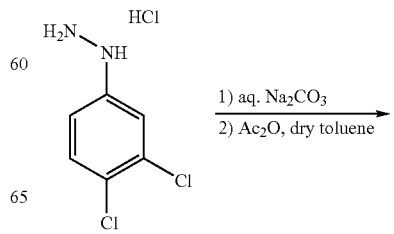

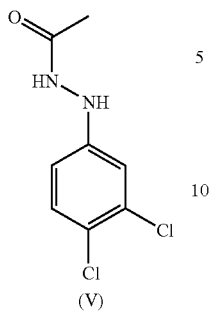

(V)

N'-(3,4-Dichlorophenyl)hydrazine was liberated from its hydrochloride (10.0 g, 46.8 mmol) by partitioning the solid between diluted Na$_2$CO$_3$ solution (10 ml saturated solution and 40 ml water) and AcOEt. The aqueous layer was extracted two more times with AcOEt, the organic extracts were dried (Na$_2$SO$_4$), the solvent was removed in vacuo, and the residue was taken up in dry toluene (100 ml). To this solution acetic anhydride (4.78 g, 46.8 mmol) was slowly added, and the reaction mixture was stirred at room temperature for 15 min. Light petroleum (50 ml) was added, the mixture was cooled in the refrigerator (−20° C.), and the resulting crystals were collected on a sintered glass funnel and washed with cold petrol ether. Recrystallization from MeOH yielded (V) (8.30 g, 81%) as shiny white crystals, mp 179-182° C. (lit. 168-171° C.). TLC CHCl$_3$/MeOH 9:1.

MS m/z (%): 222/220/218 (W, 3/22/34), 178 (64), 176 (100), 160 (20), 43 (94).

Only the NMR signals of the dominant isomer are given (ratio ca. 9:1):

$^1$H-NMR (DMSO-d$_6$): (ppm) 9.69 (d, 11-1, NH—CO, $^3$J=2.0 Hz), 8.09 (d, 1H, Ph-NH, $^3$J=2.0 Hz), 7.32 (d, 1H, Ph 1-1-5, $^3$J(H5, 1-16)=8.8 Hz), 6.83 (d, 1H, Ph H-2, $^4$J(H2, H6)=2.5 Hz), 6.66 (dd, 1H, Ph H-6, $^4$3(H2, 146) 2.5 Hz, $^3$J(H5, H6)=8.8 Hz), 1.90 (s, 31-1, Me).

$^{13}$C-NMR (DMSO-d$_6$): S (ppm) 169.2 (C=O), 149.6 (Ph C-1), 131.2 (Ph C-3), 130.5 (Ph C-5), 119.1 (Ph C-4), 112.9 (Ph C-2*), 112.4 (Ph C-6*), 20.6 (Me).

Step 2A: Synthesis of 1-(3,4-Dichlorophenyl)-5-methyl-1H-pyrazol-3-ol (VI)

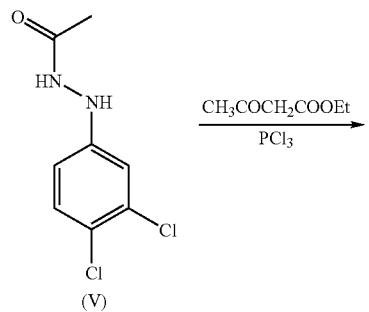

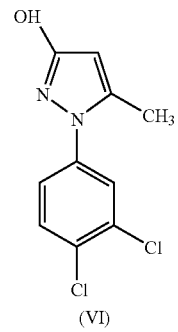

(VI)

To a mixture of (V) (5.0 g, 22.8 mmol) and ethyl acetoacetate (2.97 g 22.8 mmol) was slowly added PCl$_3$ (3.13 g, 22.8 mmol). The mixture was warmed to 50° C. for 1.5 h, poured into ice water (150 ml), and the resulting precipitate was collected on a sintered glass funnel and recrystallized from EtOH to yield (VI) (2.29 g, 41%) as white crystals, mp 208-211° C. (lit. 208-209° C.), TLC CHCl$_3$/MeOH 9:1.

MS m/z (%): 246/244/242 (M+, 11/59/100), 207 (32), 147 (20), 145 (34), 111 (20), 109 (23), 75 (20).

$^1$H-NMR (CDCl3): S (ppm) 11.72 (broad s, 1H, OH), 7.54 (d, 1H, Ph H-5, 3J(H5, H6)=8.5 Hz), 7.48 (d, 1H, Ph 11-2, 4J(H2, H6)-2.5 Hz), 7.26 (dd, 1H, Ph H-6, 4J(H2, H6)=2.5 Hz, 3J(H5, H6)=83 Hz), 5.63 (s, 1H, 4-H), 2.28 (s, 3H, 5-Me).

$^{13}$C-NMR (CDCl$_3$): 6 (ppm) 163.1 (Pz C-3), 141.2 (Pz C-5), 137.9 (Ph C-1), 133.1 (Ph C-3), 131.4 (Ph C-4), 131.0 (Ph C-5), 126.1 (Ph C-2), 123.6 (Ph C-6), 94.5 (Pz C-4), 12.7 (5-Me).

Step 3A. Synthesis of 3-(2-chloroethoxy)-1-(3,4-dichlorophenyl)-5-methyl-1H-pyrazole

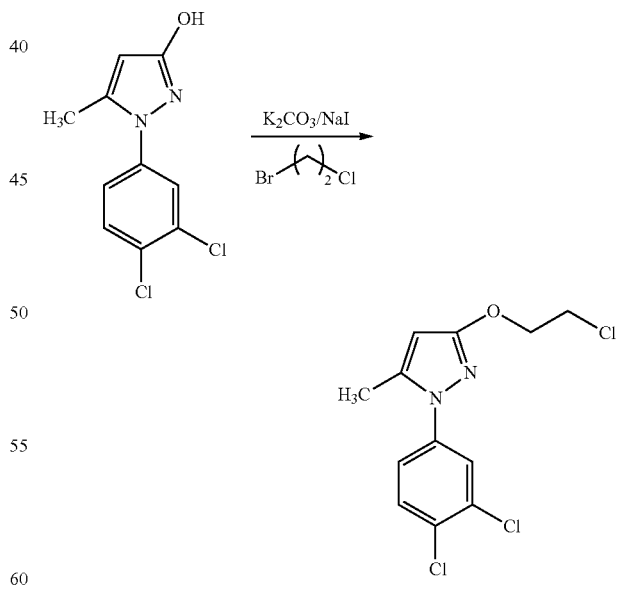

A mixture of 1-(3,4-dichlorophenyl)-5-methyl-1H-pyrazol-3-ol (0.29 g, 1.19 mmol), 1-bromo-2-chloroethane (0.2 µl, 2.4 mmol), K$_2$CO$_3$ (0.49 g, 3.6 mmol) and NaI (0.18 g, 1.19 mmol) in dry dimethylformamide (25 ml) was stirred overnight at room temperature. Solvent was evaporated in vacuo and the crude residue was partitioned between water/ dichloromethane. The organic extracts were washed with water, dried on Na$_2$SO$_4$ and concentrated in vacuo to obtain 0.33 g of an oily compound, corresponding to a mixture of 3-(2-chloroethoxy)-1-(3,4-dichlorophenyl)-5-methyl-1H-pyrazole, and starting material. Hexane was added to the mixture and stirred for 10 min., the unsoluble material, corresponding to unreacted starting compound, was filtered off, and filtrate evaporated to dryness yielding 0.19 g of 3-(2-chloroethoxy)-1-(3,4-dichlorophenyl)-5-methyl-1H-pyrazole.

$^1$H-NMR (CDCl$_3$) δ ppm: 7.55 (d, J=2.5 Hz, 1H), 7.5 (d, J=8.7 Hz, 1H), 7.3 (dd, J=2.5 and 8.7 Hz, 1H), 5.7 (s, 1H), 4.45 (t, J=5.9 Hz, 2H), 3.8 (t, J=5.9 Hz, 2H), 2.3 (s, 3H).

Step 4A. Synthesis of ethyl 4-{2-[1-(3,4-dichlorophenyl)-5-methyl-1H-pyrazol-3-yloxy]ethyl}piperazine carboxylate

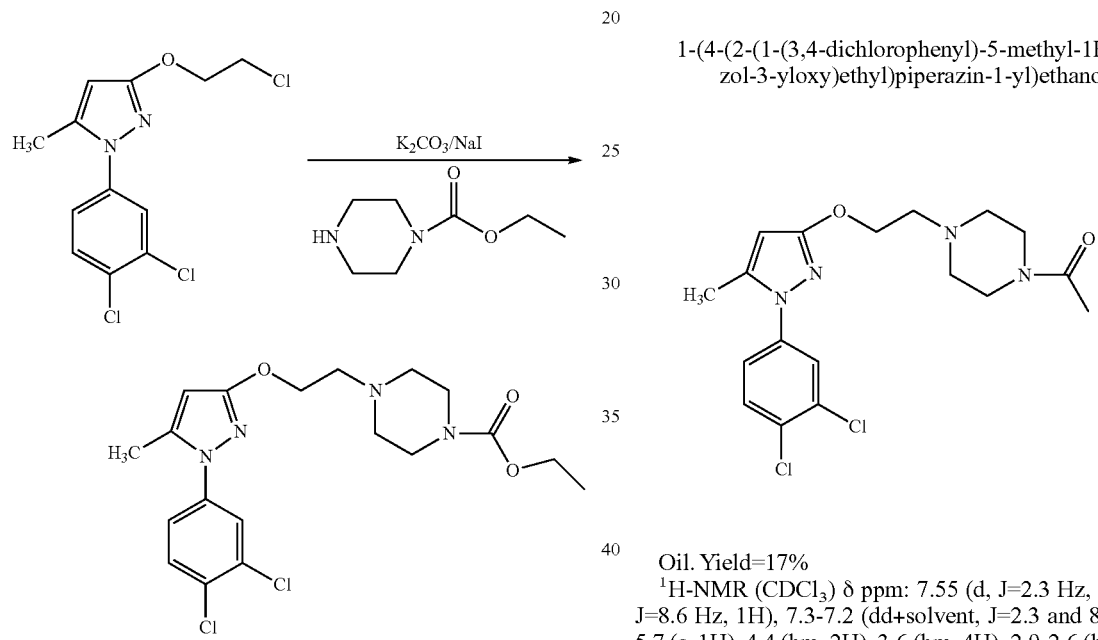

A mixture of 3-(2-chloroethoxy)-1-(3,4-dichlorophenyl)-5-methyl-1H-pyrazole (0.2 g, 0.65 mmol), ethyl piperazine-1-carboxylate (0.113 g, 0.72 mmol), K$_2$CO$_3$ (270 mg, 1.96 mmol) and NaI (98 mg, 0.65 mmol) in dry dimethylformamide (6 ml) was warmed overnight at 85° C., and then an additionally 16 hrs at 95° C., in a dry nitrogen atmosphere. Solvents were evaporated in vacuo and the crude residue partitioned in water/ethyle acetate. The combined organic extracts were washed with water, dried on Na$_2$SO$_4$ and concentrated in vacuo to obtain a crude oil, which was purified by column chromatography on silica gel (ethyl acetate/petroleum ether 8:2) yielding 69 mg of ethyl 4-{2-[1-(3,4-dichlorophenyl)-5-methyl-1H-pyrazol-3-yloxy]ethyl}piperazine carboxylate as a colourless oil $^1$H-NMR (CDCl$_3$) δ ppm: 7.55 (d, J=2.5 Hz, 1H), 7.5 (d, J=8.6 Hz, 1H), 7.3-7.2 (dd+solvent, J=2.5 and 8.6 Hz, 1H), 5.7 (s, 1H), 4.4 (bm, 2H), 4.15 (q, J=7.1 Hz, 2H), 3.6 (bm, 4H), 2.9-2.6 (bm, 6H), 2.3 (s, 3H), 1.25 (t, J=7.1 Hz, 3H).

Example 4

1-(4-(2-(1-(3,4-dichlorophenyl)-5-methyl-1H-pyrazol-3-yloxy)ethyl)piperazin-1-yl)ethanone Oil. Yield=17%

$^1$H-NMR (CDCl$_3$) δ ppm: 7.55 (d, J=2.3 Hz, 1H), 7.5 (d, J=8.6 Hz, 1H), 7.3-7.2 (dd+solvent, J=2.3 and 8.6 Hz, 1H), 5.7 (s, 1H), 4.4 (bm, 2H), 3.6 (bm, 4H), 2.9-2.6 (bm, 6H), 2.3 (s, 3H), 2.1 (s, 3H).

The following examples 5 to 13 listed in the table were all prepared in an analogous manner based on the preparation described in example 3:

| Ex. N° | Structure | Name | $^1$H-NMR δ ppm | m.p. ° C. | MS |
|---|---|---|---|---|---|
| 5 | 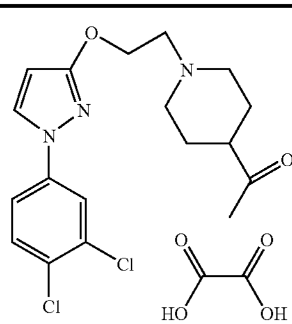 | 1-{1-[2-(1-(3,4-Dichlorophenyl)-1H-pyrazol-3-yloxy)ethyl]piperidin-4-yl}ethanone oxalate | DMSO-d$_6$: 8.5 (d, J = 2.7 Hz, 1H), 8.05 (d, J = 2.1 Hz, 1H), 7.75 (m, 2H), 6.15 (d, J = 2.7 Hz, 1H), 4.5 (t, J = 5.0 Hz, 2H), 3.3 (m, 4H), 2.8 (m, 2H), 2.1 (s, 3H), 2.0 (m, 3H), 1.6 (m, 2H). | 98-100 | 381 |

-continued

| Ex. N° | Structure | Name | ¹H-NMR δ ppm | m.p. °C. | MS |
|---|---|---|---|---|---|
| 6 | 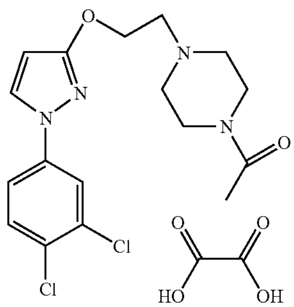 | 1-{4-[2-(1-(3,4-Dichlo-rophenyl)-1H-pyrazol-3-yloxy)ethyl]pipera-zin-1-yl}ethanone oxalate | DMSO-d₆: 8.45 (d, J = 2.6 Hz, 1H), 8.0 (d, J= 2.2 Hz, 1H), 7.75 (m, 2H), 6.1 (d, J = 2.6 Hz, 1H), 4.4 (t, J = 5.4 Hz, 2H), 3.5 (m, 4H), 3.0 (m, 2H), 2.7 (m, 4H), 2.0 (s, 3H). | 206-210 | 382 |
| 7 | 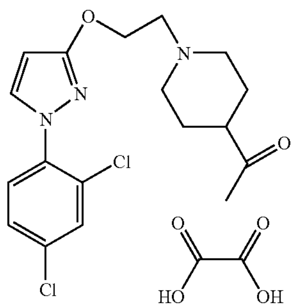 | 1-(1-[2-{1-(2,4-Dichlo-rophenyl)-1H-pyrazol-3-yloxy}ethyl]piperi-din-4-yl)ethanone oxalate | DMSO-d₆: 8.0 (d, J = 2.6 Hz, 1H), 7.85 (dd, J = 1.8, 0.7 Hz, 1H), 7.55 (m, 2H), 6.05 (d, J = 2.6 Hz, 1H), 4.4 (t, J = 5.1 Hz, 2H), 3.3-3.15 (m + H₂O, 6H), 2.45 (solv + m, 1H), 2.1 (s, 3H), 1.9 (m, 2H), 1.6 (m, 2H). | 137-140 | 381 |
| 8 | 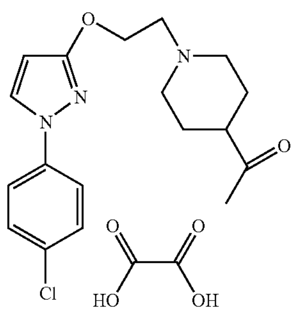 | 1-(1-(2-(1-(4-Chloro-phenyl)-1H-pyrazol-3-yloxy)ethyl)piperidin-4-yl)ethanone oxalate | DMSO: 8.45 (d, J = 2.6 Hz, 1H), 7.8 (d, J = 8.9 Hz, 2H), 7.55 (d, J = 8.9 Hz, 2H), 6.15 (d, J = 2.6 Hz, 1H), 4.5 (t, J = 5.1 Hz, 2H), 3.4-3.25 (m, 4H), 2.8 (m, 2H), 2.6 (m, 1H), 2.15 (s, 3H), 1.95 (m, 2H), 1.7 (m, 2H). | 150-153 | 347 |
| 9 | 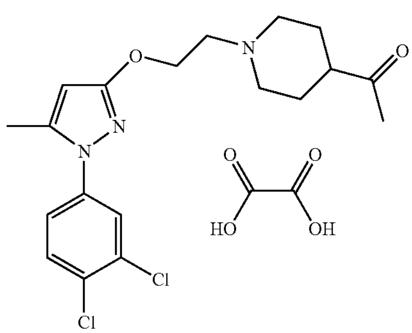 | 1-(1-(2-(1-(3,4-Dichlo-rophenyl)-5-methyl-1H-pyrazol-3-yloxy) ethyl)piperidin-4-yl)ethanone oxalate | CD₃OD: 7.7 (d, J =2.4 Hz, 1H), 7.65 (d, J = 8.89 Hz, 1H), 7.4 (dd, J = 8.8, 2.4 Hz, 1H), 5.85 (s, 1H), 4.55 (m, 2H), 3.65-3.5 (m, 4H), 3.2-3.1 (m, 2H), 2.8 (m, 1H), 2.35 (s, 3H), 2,2 (s, 3H), 2.1 (m, 2H), 1.85 (m, 2H). | 158-165 | 395 |
| 10 | 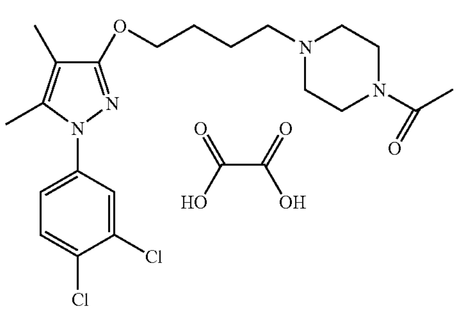 | 1-(4-(4-(1-(3,4-Dichlo-rophenyl)-4,5-dimethyl-1H-pyrazol-3-yloxy) butyl)piperazin-1-yl)ethanone oxalate | DMSO-d₆: 7.7 (d, J = 2.4 Hz, 1H), 7.65 (d, J = 8.8 Hz, 1H), 7.45 (dd, J = 2.4, 8.8 Hz, 1H), 4.15 (t, J = 5.6 Hz, 2H), 3.55 (m, 4H), 2.8 (m, 6H), 2.25 (s, 3H), 2.0 (s, 3H), 1.8 (s, 3H), 1.7 (m, 4H). | 186-188 | 438 |

-continued

| Ex. N° | Structure | Name | $^1$H-NMR δ ppm | m.p. °C | MS |
|---|---|---|---|---|---|
| 11 | 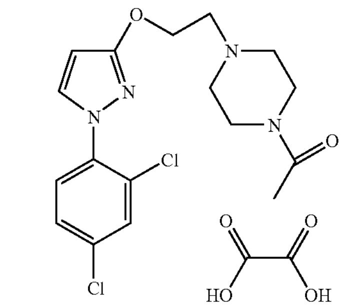 | 1-(4-(2-(1-(2,4-Dichlo-rophenyl)-1H-pyrazol-3-yloxy)ethyl)piperazin-1-yl)ethanone oxalate | DMSO-$d_6$: 8.0 (d, J = 2.6 Hz, 1H), 7.85 (d, J = 1.9 Hz, 1H), 7.55 (m, 2H), 6.05 (d, J = 2.6 Hz, 1H), 4.3 (t, J = 5.4 Hz, 2H), 3.5 (t, J = 4.8 Hz, 4H), 2.95 (t, J = 5.1 Hz, 2H), 2.65 (m, 4H), 1.95 (s, 3H). | 156-158 | 382 |
| 12 | 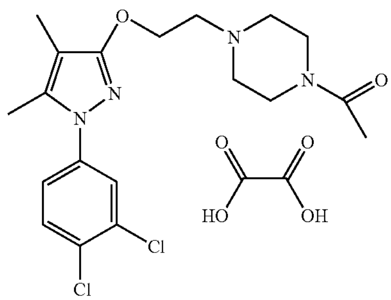 | 1-(4-(2-(1-(3,4-Dichlo-rophenyl)-4,5-dimethyl-1H-pyrazol-3-yloxy)ethyl)piperazin-1-yl)ethanone oxalate | (DMSO-$d_6$: 7.75 (d, J = 2.5 Hz, 1H), 7.7 (d, J = 8.8 Hz, 1H), 7.5 (dd, J = 2.5, 8.8 Hz, 1H), 4.35 (t, J = 5.3 Hz, 2H), 3.45-3.0 (m + $H_2O$, 4H), 2.95 (m, 2H), 2.65 (m, 4H), 2.25 (s, 3H), 1.95 (s, 3H), 1.85 (s, 3H). | 180-184 | 410 |
| 13 | 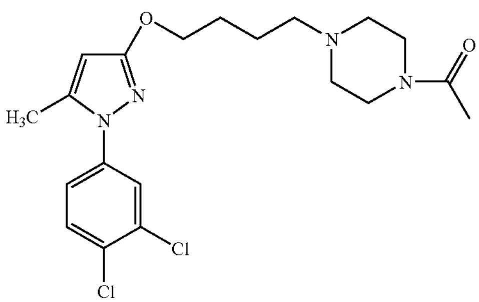 | 1-(4-{4-[1-(3,4-Dichloro-phenyl)-5-methyl-1H-pyrazol-3-yloxy]-butyl}-piperazin-1-yl)-ethanone | DMSO-$d_6$: 7.75 (d, J = 2.5 Hz, 1H), 7.7 (d, J = 8.8 Hz, 1H), 7.5 (dd, J = 2.5, 8.8 Hz, 1H), 5.8 (s, 1H), 4,1 (t, J = 5.8 Hz, 2H) 3.55 (m, 4H), 2.8 (m, 6H), 2.3 (s, 3H), 2.0 (s, 3H), 1.7 (m, 4H) | 147-150 | 424 |

Biological Activity

Some representative compounds of the invention were tested for their activity as sigma (sigma-1 and sigma-2) inhibitors. The following protocols were followed:

Sigma-1

Brain membrane preparation and binding assays for the σ1-receptor were performed as described (DeHaven-Hudkins et al., 1992) with some modifications. In brief, guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was resuspended in fresh Tris-HCl buffer (50 mM, pH 7.4) and stored on ice until use.

Each assay tube contained 10 μL of [$^3$H](+)-pentazocine (final concentration of 0.5 nM), 900 μL of the tissue suspension to a final assay volume of 1 mL and a final tissue concentration of approximately 30 mg tissue net weight/mL. Non-specific binding was defined by addition of a final concentration of 1 μM haloperidol. All tubes were incubated at 37° C. for 150 min before termination of the reaction by rapid filtration over Schleicher & Schuell GF 3362 glass fibre filters [previously soaked in a solution of 0.5% polyethylenimine for at least 1 h]. Filters were then washed with four times with 4 mL of cold Tris-HCl buffer (50 mM, pH 7.4). Following addition of scintillation cocktail, the samples were allowed to equilibrate overnight. The amount of bound radioactivity was determined by liquid scintillation spectrometry using a Wallac Winspectral 1414 liquid scintillation counter. Protein concentrations were determined by the method of Lowry et al. (1951).

Sigma-2

Binding studies for σ2-receptor are performed as described (Radesca et al., 1991) with some modifications. In brief, brains from sigma receptor type I (σ1) knockout mice are homogenized in a volume of 10 mL/g tissue net weight of ice-cold 10 mM Tris-HCl, pH 7.4, containing 320 mM sucrose (Tris-sucrose buffer) with a Potter-Elvehjem homogenizer (10 strokes at 500 r.p.m.) The homogenates are then centrifuged at 1000 g for 10 min at 4° C., and the supernatants are saved. The pellets are resuspended by vortexing in 2 mL/g ice-cold Tris-sucrose buffer and centrifuged again at 1000 g for 10 min. The combined 1000 g supernatants are centrifuged at 31000 g for 15 min at 4° C. The pellets are resuspended by vortexing in 3 mL/g 10 mM Tris-HCl, pH 7.4, and the suspension is kept at 25° C. for 15 min. Following centrifugation at 31000 g for 15 min, the pellets are resuspended by gentle Potter Elvehjem homogenization to a volume of 1.53 mL/g in 10 mM Tris-HCl pH 7.4.

The assay tubes contain 10 μL of [$^3$H]-DTG (final concentration of 3 nM), 400 μL of the tissue suspension (5.3 mL/g in 50 mM Tris-HCl, pH 8.0) to a final assay volume of 0.5 mL. Non-specific binding is defined by addition of a final concentration of 1 μM haloperidol. All tubes are incubated at 25° C. for 120 min before termination of the reaction by rapid filtration over Schleicher & Schuell GF 3362 glass fibre filters [previously soaked in a solution of 0.5% polyethylenimine for at least 1 h]. Filters are washed three times with 5 mL volumes of cold Tris-HCl buffer (10 mM, pH 8.0). Following addition of scintillation cocktail samples are allowed to equilibrate overnight. The amount of bound radioactivity is determined by liquid scintillation spectrometry using a Wallac Winspectral 1414 liquid scintillation counter. Protein concentrations are determined by the method of Lowry et al. (1951).

REFERENCES

DeHaven-Hudkins, D. L., L. C. Fleissner, and F. Y. Ford-Rice, 1992, "Characterization of the binding of [$^3$H](+)pentazocine to σ a recognition sites in guinea pig brain", *Eur. J. Pharmacol.* 227, 371-378.

Radesca, L., W. D. Bowen, and L. Di Paolo, B. R. de Costa, 1991, Synthesis and Receptor Binding of Enantiomeric N-Substituted cis-N-[2-(3,4-Dichlorophenyl)ethyl]-2-(1-pyrrolidinyl)cyclohexylamines as High-Affinity σ Receptor Ligands, *J. Med. Chem.* 34, 3065-3074.

Langa, F., Codony X., Tovar V., Lavado A., Giménez E., Cozar P., Cantero M., Dordal A., Hernández E., Pérez R., Monroy X., Zamanillo D., Guitart X., Montoliu Ll., 2003, Generation and phenotypic analysis of sigma receptor type I (Sigma1) knockout mice, *European Journal of Neuroscience*, Vol. 18, 2188-2196.

Lowry, O. H., N. J. Rosebrough, A. L. Farr, and R. J. Randall, 1951, Protein measurement with the Folin phenol reagent, *J. Biol. Chem.*, 193, 265.

Some of the results obtained for the Sigma-1 Receptor are shown in table (I).

TABLE (I)

| Example | % Binding σ1 $10^{-7}$M | % Binding σ1 $10^{-8}$M | $K_i$ [nM] |
|---------|---------|---------|---------|
| 1 | 94.4 | 49.4 | |
| 2 | 90.7 | 53.2 | |
| 3 | 99.5 | 58.4 | |
| 4 | 99.4 | 82.5 | |
| 5 | | | 1.3 ± 0.4 |
| 6 | | | 4.2 |
| 7 | | | 1.5 |
| 8 | | | 1.3 |
| 9 | | | 8.3 |

In-Vivo-Experiments Using Von Frey Filaments in a Model of Capsaicine—Induced Allodynia:

This model is described in detail in the experimental part of WO 2006/010587 A1, examples 1 and 2, the description being included here by reference. Capsaicin is thereby injected into experimental animals to produce acute pain followed by allodynia.

Briefly after habituation mice were first treated with the test-compound (or not in controls). Then capsaicin (1% DMSO) is injected into their paw resulting in developing pain in the effected paw. The effected paw is then treated with a mechanical stimulus and the latency time before the paw is withdrawn is measured.

The compound according to example 6 was tested and 77% analgesia was achieved at a capsaicin concentration of 16 mg.

The invention claimed is:
1. A compound of the formula I:

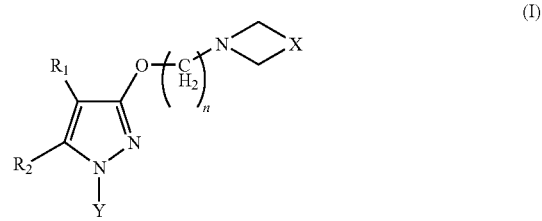

wherein
$R_1$ is selected from the group formed by hydrogen, substituted or unsubstituted alkyl, substituted or unsubstituted cycloalkyl, substituted or unsubstituted aryl, substituted or unsubstituted alkenyl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$—$C$=$NR_8$, —CN, —$OR_8$, —$OC(O)R_8$, —$NR_8R_9$, —$NR_8C(O)R_9$, —$NO_2$, —N=$CR_8R_9$, or halogen;

$R_2$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$—$C$=$NR_8$, —CN, —$OR_8$, —$OC(O)R_8$, —$S(O)_t$—$R_8$, —$NR_8R_9$, —$NR_8C(O)R_9$, —$NO_2$, —N=$CR_8R_9$, or halogen;

Y is selected from substituted or unsubstituted phenyl or naphtyl;
X is selected from:
—$CH_2$-Het-$CHR_x$—,
—$CH_2$—$CHR_x$-Het-,
-Het-$CH_2$—$CHR_x$—,
—$CH_2$—$CH_2$—$CHR_x$—, or
—$CH_2$—$CHR_x$—$CH_2$—,
with
Het being NH, S or O,
—$CHR_x$— being

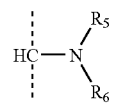

with
$R_5$ and $R_6$, identical or different, represent a hydrogen atom; an optionally substituted $C_{1-4}$ alkyl group; an optionally substituted aryl group; an optionally substituted heteroaryl group; a $C_{1-4}$ alkoxy group; a benzyl group; a phenethyl group;
or
form, together with their bridging nitrogen atom, an optionally substituted heteroaryl group which is optionally condensed to other, optionally at least one heteroatom containing mono- or polycyclic ring system which is optionally at least mono-substituted;

or

X is selected from:
—CH$_2$-Het-CHR$_x$—,
—CH$_2$—CHR$_x$-Het-,
-Het-CH$_2$—CHR$_x$—,
—CH$_2$—CH$_2$—CHR$_x$—,
—CH$_2$—CHR$_x$—CH$_2$,
—CH$_2$—CH$_2$—NR$_x$—, or,
—CH$_2$—NR$_x$—CH$_2$—,
with
Het being NH, S or O,
R$_x$ being a —(C=O)—R$^{10}$; or a —(C=O)—O—R$^{11}$ group; wherein
R$^{10}$ and R$^{11}$ independently represent a hydrogen atom; a saturated or unsaturated, optionally at least mono-substituted C$_{1-6}$ alkyl group; an optionally at least mono-substituted aryl group; an optionally at least mono-substituted heteroaryl group; an optionally at least mono-substituted, optionally at least one heteroatom as ring member containing cycloalkyl group; a saturated or unsaturated, optionally at least mono-substituted C$_{1-6}$ alkyl-aryl group; a saturated or unsaturated, optionally at least mono-substituted C$_{1-6}$ alkyl-heteroaryl group; or a saturated or unsaturated, optionally at least mono-substituted C$_{1-6}$ alkyl-cycloalkyl group wherein the cycloalkyl group contains optionally at least one heteroatom as ring member;

n is selected from 1, 2, 3, 4, 5, 6, 7 or 8;
t is 1, 2 or 3;
R$_8$ and R$_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, or halogen;
optionally in form of a racemate in any mixing ratio, or a corresponding salt thereof.

2. A compound according to claim 1 of the formula IB:

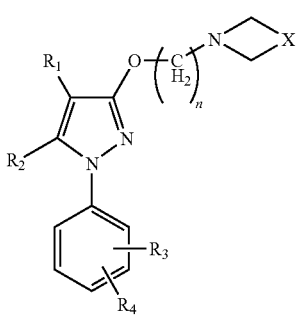

(IB)

wherein
R$_1$ is selected from the group formed by hydrogen; substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted aromatic heterocyclyl, substituted or unsubstituted heterocyclyl, substituted or unsubstituted heterocyclylalkyl, —COR$_8$, —C(O)OR$_8$, —C(O)NR$_8$R$_9$—C=NR$_8$, —CN, —OR$_8$, —OC(O)R$_8$, —NR$_8$R$_9$, —NR$_8$C(O)R$_9$, —NO2, —N=CR$_8$R$_9$ or halogen, R$_2$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —COR$_8$, —C(O)OR$_8$, —C(O)NR$_8$R$_9$—C=NR$_8$, —CN, —OR$_8$, —OC(O)R$_8$, —S(O)$_t$—R$_8$, —NR$_8$R$_9$, —NR$_8$C(O)R$_9$, —NO$_2$, —N=CR$_8$R$_9$, or halogen;

R$_3$ and R$_4$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —COR$_8$, —C(O)OR$_8$, —C(O)NR$_8$R$_9$—C=NR$_8$, —CN, —OR$_8$, —OC(O)R$_8$, —S(O)$_t$—R$_8$, —NR$_8$R$_9$, —NR$_8$C(O)R$_9$, —NO2, —N=CR$_8$R$_9$, or halogen, or together with the phenyl ring to which they are attached they form a substituted or unsubstituted naphthyl ring, X is selected from:
—CH$_2$-Het-CHR$_x$—,
—CH$_2$—CHR$_x$-Het-,
-Het-CH$_2$—CHR$_x$—,
—CH$_2$—CH$_2$—CHR$_x$—, or
—CH$_2$—CHR$_x$—CH$_2$-,
with
Het being NH, S or O,
—CHR$_x$— being

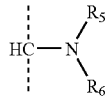

wherein
R$_5$ and R$_6$, identical or different, represent a hydrogen atom; an optionally substituted C$_{1-4}$ alkyl group; an optionally substituted aryl group; an optionally substituted heteroaryl group; a C$_{1-4}$ alkoxy group; a benzyl group; a phenethyl group;

or form, together with their bridging nitrogen atom, an optionally substituted heteroaryl group which is optionally condensed to other, optionally at least one heteroatom containing mono- or polycyclic ring system which is optionally at least mono-substituted;

or

X is selected from:
—CH$_2$-Het-CHR$_x$—,
—CH$_2$—CHR$_x$-Het-,
-Het-CH$_2$—CHR$_x$—,
—CH$_2$—CH$_2$—CHR$_x$—,
—CH$_2$—CHR$_x$—CH$_2$—,
—CH$_2$—CH$_2$—NR$_x$—, or
—CH$_2$—NR$_x$—CH$_2$—,
with
Het being NH, S or O,
R$_x$ being a —(C=O)—R$^{10}$; or a —(C=O)—O—R$^{11}$ group; wherein
R$^{10}$ and R$^{11}$ independently represent a hydrogen atom; a saturated or unsaturated, optionally at least mono-substituted C$_{1-6}$ alkyl group; an optionally at least mono-substituted aryl group; an optionally at least mono-substituted heteroaryl group; an optionally at least mono-substituted, optionally at least one heteroatom as ring member containing cycloalkyl group; a saturated or unsaturated, optionally at least mono-substituted $C_{1-6}$ alkyl-aryl group; a saturated or unsaturated, optionally at least mono-substituted $C_{1-6}$ alkyl-heteroaryl group; or a saturated or unsaturated, optionally at least mono-substituted $C_{1-6}$ alkyl-cycloalkyl group wherein the cycloalkyl group contains optionally at least one heteroatom as ring member;

n is selected from 1, 2, 3, 4, 5, 6, 7 or 8;

t is 1, 2 or 3;

$R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, or halogen;

optionally in form of a racemate in any mixing ratio, or a corresponding salt thereof.

3. A compound according to claim 1 of the formula I:

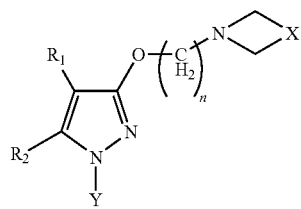

(I)

wherein $R_1$ is selected from the group formed by hydrogen, substituted or unsubstituted alkyl, substituted or unsubstituted cycloalkyl, substituted or unsubstituted aryl, substituted or unsubstituted alkenyl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$—$C=NR_8$, —CN, —$OR_8$, —$OC(O)R_8$, —$NR_8R_9$, —$NR_8C(O)R_9$, —$NO_2$, —$N=CR_8R_9$, or halogen;

$R_2$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$—$C=NR_8$, —CN, —$OR_8$, —$OC(O)R_8$, —$S(O)_t$—$R_8$, —$NR_8R_9$, —$NR_8C(O)R_9$, —$NO_2$, —$N=CR_8R_9$, or halogen;

Y is selected from substituted or unsubstituted phenyl or naphtyl;

X is selected from:
—$CH_2$-Het-$CHR_x$—,
—$CH_2$—$CHR_x$-Het-,
-Het-$CH_2$—$CHR_x$—,
—$CH_2$—$CH_2$—$CHR_x$—, or
—$CH_2$—$CHR_x$—$CH_2$-,
with
Het being NH, S or O,
—$CHR_x$— being

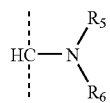

wherein $R_5$ and $R_6$, identical or different, represent a hydrogen atom; an optionally substituted $C_{1-4}$ alkyl group; an optionally substituted aryl group; an optionally substituted heteroaryl group; a $C_{1-4}$ alkoxy group; a benzyl group; a phenethyl group;

or form, together with their bridging nitrogen atom, an optionally substituted heteroaryl group which is optionally condensed to other, optionally at least one heteroatom containing mono- or polycyclic ring system which is optionally at least mono-substituted;

n is selected from 1, 2, 3, 4, 5, 6, 7 or 8;

t is 1, 2, or 3;

$R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, or halogen;

optionally in form of a racemate in any mixing ratio, or a corresponding salt thereof.

4. A compound according to claim 2 of the formula IB:

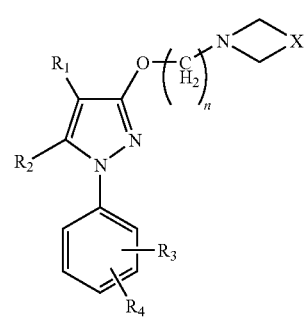

(IB)

wherein $R_1$ is selected from the group formed by hydrogen; substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted aromatic heterocyclyl, substituted or unsubstituted heterocyclyl, substituted or unsubstituted heterocyclylalkyl, —$COR_8$, —$C(O)OR_8$, —$C(O)NR_8R_9$—$C=NR_8$, —CN, —$OR_8$, —$OC(O)R_8$, —$NR_8R_9$, —$NR_8C(O)R_9$, —NO2, —$N=CR_8R_9$ or halogen, $R_2$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$—$C=NR_8$, —CN, —$OR_8$, —$OC(O)R_8$, —$S(O)_t$—$R_8$, —$NR_8R_9$, —$NR_8C(O)R_9$, —$NO_2$, —$N=CR_8R_9$, or halogen;

$R_3$ and $R_4$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$—$C=NR_8$, —CN, —$OR_8$, —$OC(O)R_8$, —S(O)$_t$—R$_8$, —NR$_8$R$_9$, —NR$_8$C(O)R$_9$, —NO2, —N=CR$_8$R$_9$, or halogen, or together with the phenyl ring to which they are attached they form a substituted or unsubstituted naphthyl ring, X is selected from:
- —CH$_2$-Het-CHR$_x$—,
- —CH$_2$—CHR$_x$-Het-,
- -Het-CH$_2$—CHR$_x$—,
- —CH$_2$—CH$_2$—CHR$_x$—, or
- —CH$_2$—CHR$_x$—CH$_2$—, with Het being NH, S or O, —CHR$_x$— being

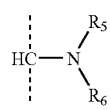

with

R$_5$ and R$_6$, identical or different, represent a hydrogen atom; an optionally substituted C$_{1-4}$ alkyl group; an optionally substituted aryl group; an optionally substituted heteroaryl group; a C$_{1-4}$ alkoxy group; a benzyl group; a phenethyl group;

or form, together with their bridging nitrogen atom, an optionally substituted heteroaryl group which is optionally condensed to other, optionally at least one heteroatom containing mono- or polycyclic ring system which is optionally at least mono-substituted;

n is selected from 1, 2, 3, 4, 5, 6, 7 or 8;

t is 1, 2 or 3;

R$_8$ and R$_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, or halogen;

optionally in form of a racemate in any mixing ratio, or a corresponding salt thereof.

5. A compound according to claim 1 of the formula I:

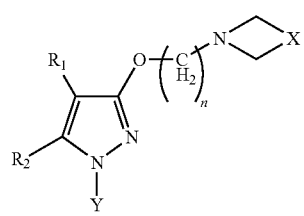

(I)

wherein

R$_1$ is selected from the group formed by hydrogen, substituted or unsubstituted alkyl, substituted or unsubstituted cycloalkyl, substituted or unsubstituted aryl, substituted or unsubstituted alkenyl, substituted or unsubstituted arylalkyl, substituted or unsubstituted heterocyclyl, substituted or unsubstituted heterocyclylalkyl, —COR$_8$, —C(O)OR$_8$, —C(O)NR$_8$R$_9$—C=NR$_8$, —CN, —OR$_8$, —OC(O)R$_8$, —NR$_8$R$_9$, —NR$_8$C(O)R$_9$, —NO$_2$, —N=CR$_8$R$_9$, or halogen;

R$_2$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —COR$_8$, —C(O)OR$_8$, —C(O)NR$_8$R$_9$—C=NR$_8$, —CN, —OR$_8$, —OC(O)R$_8$, —S(O)$_t$—R$_8$, —NR$_8$R$_9$, —NR$_8$C(O)R$_9$, —NO$_2$, —N=CR$_8$R$_9$, or halogen;

Y is selected from substituted or unsubstituted phenyl or naphtyl;

X is selected from:
- —CH$_2$-Het-CHR$_x$—,
- —CH$_2$—CHR$_x$-Het-,
- -Het-CH$_2$—CHR$_x$—,
- —CH$_2$—CH$_2$—CHR$_x$—,
- —CH$_2$—CHR$_x$—CH$_2$—,
- —CH$_2$—CH$_2$—NR$_x$—, or
- —CH$_2$—NR$_x$—CH$_2$—, with Het being NH, S or O, R$_x$ being a —(C=O)—R$^{10}$; or a —(C=O)—O—R$^{11}$ group;

and

R$^{10}$ and R$^{11}$ independently represent a hydrogen atom; a saturated or unsaturated, optionally at least mono-substituted C$_{1-6}$ alkyl group; an optionally at least mono-substituted aryl group; an optionally at least mono-substituted heteroaryl group; an optionally at least mono-substituted, optionally at least one heteroatom as ring member containing cycloalkyl group; a saturated or unsaturated, optionally at least mono-substituted C$_{1-6}$ alkyl-aryl group; a saturated or unsaturated, optionally at least mono-substituted C$_{1-6}$ alkyl-heteroaryl group; or a saturated or unsaturated, optionally at least mono-substituted C$_{1-6}$ alkyl-cycloalkyl group wherein the cycloalkyl group contains optionally at least one heteroatom as ring member;

n is selected from 1, 2, 3, 4, 5, 6, 7 or 8;

t is 1, 2 or 3;

R$_9$ and R$_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, or halogen;

optionally in form of a racemate in any mixing ratio, or a corresponding salt thereof.

6. A compound according to claim 2 of the formula IB:

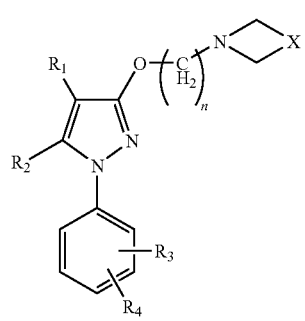

(IB)

wherein

R$_1$ is selected from the group formed by hydrogen; substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted aromatic heterocyclyl, substituted or unsubstituted heterocyclyl, substituted or unsubstituted heterocyclylalkyl, —$COR_8$, —$C(O)OR_8$, —$C(O)NR_8R_9$ —C=$NR_8$, —CN, —$OR_8$, —$OC(O)R_8$, —$NR_8R_9$, —$NR_8C(O)R_9$, —NO2, —N=$CR_8R_9$ or halogen, $R_2$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$—C=$NR_8$, —CN, —$OR_8$, —$OC(O)R_8$, —$S(O)_t$—$R_8$, —$NR_8R_9$, —$NR_8C(O)R_9$, —$NO_2$, —N=$CR_8R_9$, or halogen;

$R_3$ and $R_4$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$—C=$NR_8$, —CN, —$OR_8$, —$OC(O)R_8$, —$S(O)_t$—$R_8$, —$NR_8R_9$, —$NR_8C(O)R_9$, —NO2, —N=$CR_8R_9$, or halogen, or together with the phenyl ring to which they are attached they form a substituted or unsubstituted naphthyl ring, X is selected from:
—$CH_2$-Het-$CHR_x$—,
—$CH_2$—$CHR_x$-Het-,
-Het-$CH_2$—$CHR_x$—,
—$CH_2$—$CH_2$—$CHR_x$—,
—$CH_2$—$CHR_x$—$CH_2$—,
—$CH_2$—$CH_2$—$NR_x$—, or
—$CH_2$—$NR_x$—$CH_2$—,
with
Het being NH, S or O,
$R_x$ being a —(C=O)—$R^{10}$; or a —(C=O)—O—$R^{11}$ group;
and
$R^{10}$ and $R^{11}$ independently represent a hydrogen atom; a saturated or unsaturated, optionally at least mono-substituted $C_{1-6}$ alkyl group; an optionally at least mono-substituted aryl group; an optionally at least mono-substituted heteroaryl group; an optionally at least mono-substituted, optionally at least one heteroatom as ring member containing cycloalkyl group; a saturated or unsaturated, optionally at least mono-substituted $C_{1-6}$ alkyl-aryl group; a saturated or unsaturated, optionally at least mono-substituted $C_{1-6}$ alkyl-heteroaryl group; or a saturated or unsaturated, optionally at least mono-substituted $C_{1-6}$ alkyl-cycloalkyl group wherein the cycloalkyl group contains optionally at least one heteroatom as ring member;
n is selected from 1, 2, 3, 4, 5, 6, 7 or 8;
t is 1, 2 or 3;
$R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, or halogen;
optionally in form of a racemate in any mixing ratio, or a corresponding salt thereof.

7. A compound according to claim 1, characterized in that $R_1$ is selected from H, halogen, —$COR_8$, or substituted or unsubstituted alkyl, preferably it is selected from H, Cl, methyl or acetyl.

8. A compound according to claim 1, characterized in that $R_1$ is hydrogen.

9. A compound according to claim 1, characterized in that $R_2$ is H, aryl, $C(O)OR_8$ or alkyl, preferably methyl, iso-propyl, phenyl, C(O)O—$C_2H_5$ or H.

10. A compound according to claim 2, characterized in that $R_3$ and $R_4$ are situated in the meta and para positions of the phenyl group.

11. A compound according to claim 2, characterized in that $R_3$ and $R_4$ are independently selected from halogen, hydrogen, alkoxy, or substituted or unsubstituted alkyl, more preferably selected from hydrogen, halogen, Cl, methoxy or haloalkyl.

12. A compound according to claim 2, characterized in that $R_3$ and $R_4$ together with the phenyl ring to which they are attached form a substituted or unsubstituted naphthyl-radical.

13. A compound according to claim 1, characterized in that n is selected from 2, 3 and 4.

14. A compound according to claim 1, characterized in that X is selected from the group consisting of
—$CH_2$—$CH_2$—$CHR_x$—, and
—$CH_2$—$CHR_x$—$CH_2$-.

15. A compound according to claim 1, characterized in that $R_5$ and $R_6$ are selected from hydrogen or alkyl
or
form, together with their bridging nitrogen atom, an optionally substituted heteroaryl group which is optionally condensed to other, optionally at least one heteroatom containing mono- or polycyclic ring system which is optionally at least mono-substituted, especially an indazole or an 1H-indazole.

16. A compound according to claim 1, characterized in that the compound is selected from the group consisting of
3-{1-[2-(1-(3,4-Dichlorophenyl)-5-methyl-1H-pyrazol-3-yloxy)ethyl]piperidin-4-yl}-3H-imidazo[4,5-b]pyridine,
3-{1-[2-(1-(3,4-Dichlorophenyl)-5-methyl-1H-pyrazol-3-yloxy)ethyl]piperidin-4-yl}-3H-imidazo[4,5-b]pyridine oxalate,
optionally in form of a racemate in any mixing ratio, or a corresponding salt thereof.

17. A compound according to claim 1, characterized in that X is selected from the group consisting of
—$CH_2$—$CH_2$—$NR_x$—, and
—$CH_2$—$NR_x$—$CH_2$—.

18. A compound according to claim 1, characterized in that $R_{10}$ and $R_{11}$ are independently selected from hydrogen or alkyl.

19. A compound according to claim 1, characterized in that the compound is selected from the group consisting of
1-(4-(2-(1-(3,4-dichlorophenyl)-5-methyl-1H-pyrazol-3-yloxy)ethyl)piperazin-1-yl)ethanone,
1-(4-(2-(1-(3,4-dichlorophenyl)-5-methyl-1H-pyrazol-3-yloxy)ethyl)piperazin-1-yl)ethanone oxalate,
1-{1-[2-(1-(3,4-Dichlorophenyl)-1H-pyrazol-3-yloxy)ethyl]piperidin-4-yl}ethanone,
1-{1-[2-(1-(3,4-Dichlorophenyl)-1H-pyrazol-3-yloxy)ethyl]piperidin-4-yl}ethanone oxalate,
1-{4-[2-(1-(3,4-Dichlo-rophenyl)-1H-pyrazol-3-yloxy)ethyl]piperazin-1-yl}ethanone,
1-{4-[2-(1-(3,4-Dichlo-rophenyl)-1H-pyrazol-3-yloxy)ethyl]piperazin-1-yl}ethanone oxalate 1-(1-[2-{1-(2,4-Dichlo-rophenyl)-1H-pyrazol-3-yloxy}ethyl]piperidin-4-yl)ethanone,
1-(1-[2-{1-(2,4-Dichlo-rophenyl)-1H-pyrazol-3-yloxy}ethyl]piperidin-4-yl)ethanone oxalate,
1-(1-(2-(1-(4-Chloro-phenyl)-1H-pyrazol-3-yloxy)ethyl)piperidin-4-yl)ethanone,
1-(1-(2-(1-(4-Chloro-phenyl)-1H-pyrazol-3-yloxy)ethyl)piperidin-4-yl)ethanone oxalate,
1-(1-(2-(1-(3,4-Dichlo-rophenyl)-5-methyl-1H-pyrazol-3-yloxy)ethyl)piperidin-4-yl)ethanone,
1-(1-(2-(1-(3,4-Dichlo-rophenyl)-5-methyl-1H-pyrazol-3-yloxy)ethyl)piperidin-4-yl)ethanone oxalate,
1-(4-(4-(1-(3,4-Dichlo-rophenyl)-4,5-dimethyl-1H-pyrazol-3-yloxy)butyl)piperazin-1-yl)ethanone,
1-(4-(4-(1-(3,4-Dichlo-rophenyl)-4,5-dimethyl-1H-pyrazol-3-yloxy)butyl)piperazin-1-yl)ethanone oxalate,
1-(4-(2-(1-(2,4-Dichlo-rophenyl)-1H-pyrazol-3-yloxy)ethyl)piperazin-1-yl)ethanone,
1-(4-(2-(1-(2,4-Dichlo-rophenyl)-1H-pyrazol-3-yloxy)ethyl)piperazin-1-yl)ethanone oxalate;
1-(4-(2-(1-(3,4-Dichlo-rophenyl)-4,5-dimethyl-1H-pyrazol-3-yloxy)ethyl)piperazin-1-yl)ethanone,
1-(4-(2-(1-(3,4-Dichlo-rophenyl)-4,5-dimethyl-1H-pyrazol-3-yloxy)ethyl)piperazin-1-yl)ethanone oxalate,
1-(4-{4-[1-(3,4-Dichloro-phenyl)-5-methyl-1H-pyrazol-3-yloxy]-butyl}-piperazin-1-yl)-ethanone and
1-(4-{4-[1-(3,4-Dichloro-phenyl)-5-methyl-1H-pyrazol-3-yloxy]-butyl}-piperazin-1-yl)-ethanone oxalate;
optionally in form of a racemate in any mixing ratio, or a corresponding salt thereof.

20. A pharmaceutical composition which comprises a compound as defined in claim 1 or a pharmaceutically acceptable salt thereof, and a pharmaceutically acceptable carrier, adjuvant or vehicle.

* * * * *